(12) United States Patent
Blanchard et al.

(10) Patent No.: US 11,814,349 B1
(45) Date of Patent: Nov. 14, 2023

(54) PROCESSES FOR ORGANIC ACID ALKYL ESTER PRODUCTION USING LOW PRESSURE ALKYLATION

(71) Applicant: INVENTURE RENEWABLES, INC., Tuscaloosa, AL (US)

(72) Inventors: Cory O'Neil Blanchard, Birmingham, AL (US); Ryan Alexander Long, Hoover, AL (US); William Rusty Sutterlin, Hoover, AL (US); Timothy Nelson Brown, Tuscaloosa, AL (US); Endre Mihaly, Tuscaloosa, AL (US)

(73) Assignee: INVENTURE RENEWABLES, INC., Tuscaloosa, AL (US)

( * ) Notice: Subject to any disclaimer, the term of this patent is extended or adjusted under 35 U.S.C. 154(b) by 0 days.

(21) Appl. No.: 17/880,483

(22) Filed: Aug. 3, 2022

(51) Int. Cl.
   C07C 67/08     (2006.01)
   B01J 31/02     (2006.01)
   B01J 31/22     (2006.01)

(52) U.S. Cl.
   CPC .......... C07C 67/08 (2013.01); B01J 31/0212 (2013.01); B01J 31/2208 (2013.01);
   (Continued)

(58) Field of Classification Search
   CPC .. C07C 67/08; C07C 2601/20; B01J 31/0212; B01J 31/2208; B01J 2231/49; B01J 2531/48; B01J 2531/49; B01J 2531/842
   See application file for complete search history.

(56) References Cited

U.S. PATENT DOCUMENTS

| | | | | |
|---|---|---|---|---|
| 4,118,407 A | * | 10/1978 | Red | C11B 13/02 554/178 |
| 7,700,793 B2 | * | 4/2010 | Iyer | C11C 3/003 554/174 |

(Continued)

FOREIGN PATENT DOCUMENTS

| | | | |
|---|---|---|---|
| BY | 15811 | * | 4/2012 |
| CN | 202297557 | | 7/2012 |

(Continued)

OTHER PUBLICATIONS

Chernova et al. (UPLC-MS Triglyceride Profiling in Sunflower and Rapeseed Seeds, Biomolecules, 9, pp. 1-10, Published 2019) (Year: 2019).*

(Continued)

Primary Examiner — Jafar F Parsa
Assistant Examiner — Blaine G Doletski
(74) Attorney, Agent, or Firm — Greer, Burns & Crain, LTD; Gregory P. Einhorn

(57) ABSTRACT

Provided are industrial processes for producing an organic acid alky ester from a feedstock containing organic acids and/or saponifiables, comprising: countercurrently contacting a feedstock with an organic alkylating reagent over two or more vessels or stages at temperature between 100° C. and 400° C. and pressure between barg and 355 barg while simultaneously removing water and/or glycerin with unreacted alkylating reagent from the final vessel or stage to result in a first reaction method product containing organic acid alkyl esters, followed by a choice of using the alkyl esters as-is, purifying the organic acid alkyl esters from the first reaction product mixture or subjecting the first reaction product mixture to an additional transesterification reaction to convert saponifiables into additional organic acid alkyl (Continued)

esters, then purifying the organic acid alkyl esters from this second reaction method product.

46 Claims, 4 Drawing Sheets

(52) U.S. Cl.
CPC ........ *B01J 2231/49* (2013.01); *B01J 2531/48* (2013.01); *B01J 2531/49* (2013.01); *B01J 2531/842* (2013.01); *C07C 2601/20* (2017.05)

(56) References Cited

U.S. PATENT DOCUMENTS

| | | | |
|---|---|---|---|
| 2008/0227994 | A1* | 9/2008 | Glasl ................ C07C 67/08 554/170 |
| 2012/0103790 | A1 | 5/2012 | Krull et al. |
| 2012/0288906 | A1* | 11/2012 | Josten ............... C07C 67/08 554/170 |
| 2016/0194267 | A1 | 7/2016 | Backes et al. |

FOREIGN PATENT DOCUMENTS

| | | | |
|---|---|---|---|
| CN | 203079938 | | 7/2013 |
| CN | 104152275 | | 11/2014 |
| CN | 105907481 | | 8/2016 |
| CN | 108949365 | | 12/2018 |
| CN | 110790668 | | 2/2020 |
| GB | 1370411 | | 10/1974 |
| KR | 19950001683 | * | 2/1995 |
| WO | WO2006121021 | * | 11/2006 |
| WO | WO2007117096 | * | 10/2007 |

OTHER PUBLICATIONS

KR19950001683 translated 4 pages (Year: 1995).*
BY15811 9 pages (Year: 2012).*
WO2006121021 translated (Year: 2006).*
Milbrandt et al., "Wet waste-to-energy resources in the United States" Resources, Conservation & Recycling 137 (2018) 32-47.
Biktashev et al., "Transesterification of rapeseed and palm oils in supercritical methanol and ethanol" Biomass and Bioenergy, 2011, v 35, p. 2999-3011.
Ju et al., "Synthesis of biodiesel in subcritical water and methanol" Fuel 105 (2013) 266-271.
Deshpande et al., "Status and prospects of supercritical alcohol transesterification for biodiesel production" WIREs Energy Environ 2017, e252. doi: 10.1002/wene.252.
Lee et al., "Stimulation of Lipid Extraction Efficiency from Sewage Sludge for Biodiesel Production through Hydrothermal Pretreatment" Energies 2020, 13, 6392; doi:10.3390/en13236392.
Nelson et al., "Projected availability of fats, oils, and greases in the U.S." International Council on Clean Transportation, 2016, 1-10.
Rarokar et aL, "Progress in Synthesis of Monoglycerides for Use in Food and Pharmaceuticals" J.Food Pharm.Sci. 5 (2017) 13-19.
Kolet et al., "Production of Biodiesel from Brown Grease" Catalysts 2020, 10, 1189; doi:10.3390/catal10101189.
Warren, Hugh T., "Processing advancements in the recovery of oils from vegetable oil refinery by-products" (2018). Graduate Theses and Dissertations. 17353.
Li et al., "Recent progress on biodiesel production from municipal sewage sludge" Renewable and Sustainable Energy Reviews 135 (2021) 110260.
Flexible feedstock future for biodiesel. Biofuels International. Sep./Oct. 2020.
Wang et al., "Novel biodiesel production technology from soybean soapstock" Korean J. Chem. Eng., 24(6), 1027-1030 (2007).
Makareviciene et al., "Noncatalytic Biodiesel Synthesis under Supercritical Conditions" Processes 2021, 9, 138. https://doi.org/10.3390/pr9010138.
Nagai et al., "Mechanisms and Kinetics of Noncatalytic Ether Reaction in Supercritical Water. 2. Proton-Transferred Fragmentation of Dimethyl Ether to Formaldehyde in Competition with Hydrolysis" J. Phys. Chem. A 2005, 109, 3558-3564.
Hernandez et al., "Mississippi State Biodiesel Production Project" Dave C. Swaim School of Chemical Engineering Mississippi State University. Doe Award Number: DE-FG36-04G014251.
Zeng et al., "Continuous Esterification of Free Fatty Acids in Crude Biodiesel by an Integrated Process of Supercritical Methanol and Sodium Methoxide Catalyst" Appl Biochem Biotechnol (2014) 174:1484-1495.
Thangaraj et al., "Catalysis in biodiesel production—a review" Clean Energy, 2019, vol. 3, No. 1, 2-23.
Rani et al., "Kinetics of non-catalytic esterification of free fatty acids present in jatropha oil" Journal of Oleo Science, 2016, v 65, n 5, p. 441-445.
Sakdasri et al., "A Review of Supercritical Technologies for Lipid-Based Biofuels Production: The Glycerol-free Processes" Engineering Journal, Feb. 28, 2021, v 25, n 2, p. 1-14.
Elgharbawy et al., "A Review on Biodiesel Feedstocks and Production Technologies" J. Chil. Chem. Soc., 66, N°1 (2021), p. 5098-5109.
Karmakar et al., "Accelerated conversion of waste cooking oil into biodiesel by injecting 2-propanol and methanol under superheated conditions: A novel approach" Energy Conversion and Management 247 (2021) 114733.
Da Costa et al., "Appliance of a high pressure semi-batch reactor: supercritical transesterification of soybean oil using methanol" Food Science and Technology, Food Sci. Technol, Campinas, Ahead of Print, 2019, p. 1-20.
Bassan et al., "Esterification of fatty acids with alcohols over niobium phosphate" Fuel Processing Technology 106 (2013) 619-624.
Tran et al., "Biodiesel Production from Recycled Grease Trap Waste: A Case Study in South Australia. Part 1: The Pre-Treatment of High Free Fatty Acid Feedstock" ChemistrySelect 2018, 3, 2509-2514.
Modi, "Biodiesel production using supercritical methanol" 2010, Masters Theses, 5004.
Dunn et al., "Branched-Chain Fatty Acid Methyl Esters as Cold Flow Improvers for Biodiesel" Journal of the American Oil Chemists Society, Mar. 19, 2015, DOI 10.1007/s11746-015-2643-2.
Leonard et al., "Bubble column reactors for high pressures and high temperatures operation" Chemical Engineering Research and Design, 2015.
Cho et al., "A single step non-catalytic esterification of palm fatty acid distillate (PFAD) for biodiesel production" Fuel 93 (2012) 373-380.
Brito et al., "Eco-green biodiesel production from domestic waste cooking oil by transesterification using LiOH into basic catalysts mixtures" J. Renewable Sustainable Energy 12, 043101 (2020); https://doi.org/10.1063/5.0005625.
Bae et al., "Effect of distributor type on microbubble dispersionin a pressurized bubble column" Chemical Engineering Research and Design 1 7 4 ( 2 0 2 1 ) 188-198.
Wang et al., "Effect of Weak Acids as a Catalyst on the Transesterification of Soybean Oil in Supercritical Methanol" Energy & Fuels 2008, 22, 3479-3483.
Evaluation of the application for new alternative biodiesel production process for rendered fat including Category 1 animal by-products (BDI-RepCat® process, AT), EFSA Journal 2021;19(4):6511.
Babadi et al., "Emerging technologies for biodiesel production: Processes, challenges, and opportunities" Biomass and Bioenergy 163 (2022) 106521.
Silva et al., "Esterification of Oleic Acid in a Semi-Batch Bubble Reactor for Biodiesel Production" vol. 36, No. 01, pp. 299-308, Jan.-Mar. 2019.
Meshalkin et al., "Experimentally Calculated Study of the Effectiveness on the Process of Non-Catalytic Synthesis of Biodiesel in Reactors of Various Type" Processes 2021, 9, 1488. https://doi.org/10.3390/pr9091488.

(56) References Cited

OTHER PUBLICATIONS

Dunford et al., "Biodiesel Production Techniques" Oklahoma Cooperative Extension Service • Division of Agricultural Sciences and Natural Resources.
Gebremariam et al., "Techno-economic feasibility of producing biodiesel from acidic oil using sulfuric acid and calcium oxide as catalysts" Energy Conversion and Management 171 (2018) 1712-1720.
Kocsisová et al., "High-temperature esterification of fatty acids with methanol at ambient pressure" Eur. J. Lipid Sci. Technol. 107 (2005) 87-92.
Hussain et al., "Esterification of free fatty acids: experiments, kinetic modeling, simulation & optimization" International Journal of Green Energy, 2018, vol. 15, No. 11, 629-640.
Ilham et al., "Reactivity of Triglycerides and Fatty Acids in Sub/Supercritical Dialkyl Carbonates for Biodiesel Production".
Jaya et al., "Hydrolysis reaction utilizing cavitation from high pressure water jet impinging into palm oil bath" Ain Shams Engineering Journal xxx (xxxx) xxx.
Jayakumar et al., "Heterogeneous base catalysts: Synthesis and application for biodiesel production—A review" Bioresource Technology 331 (2021) 125054.
Kuramochi et al., "Superfast Transesterification of Triolein Using Dimethyl Ether and a Method for High-Yield Transesterification" Ind. Eng. Chem. Res. 2008, 47, 10076-10079.
Kusdiana et al., "Catalytic Effect of Metal Reactor in Transesterification of Vegetable Oil" JAOCS, vol. 81, No. 1 (2004), 103-104.
Kusdiana et al., "Effects of water on biodiesel fuel production by supercritical methanol treatment" Bioresource Technology 91 (2004) 289-295.
Melero et al., "Municipal sewage sludge to biodiesel by simultaneous extraction and conversion of lipids" Energy Conversion and Management 103 (2015) 111-118.
Micic et al., "Influence of reaction conditions and type of alcohol on biodiesel yields and process economics of supercritical transesterification" Energy Conversion and Management 86 (2014) 717-726.
Wulandani et al., "Modification of Biodiesel Reactor by using of Triple Obstacle within the Bubble Column Reactor" Energy Procedia 65 ( 2015 ) 83-89.
Yamazaki et al., "Noncatalytic alcoholysis of oils for biodiesel fuel production by a semi-batch process" Japan Journal of Food Engineering, vol. 8, No. 1, pp. 11-18, Mar. 2007.
Hagiwara et al., "Non-catalytic alcoholysis process for production of biodiesel fuel by using bubble column reactor" Journal of Physics: Conference Series 596 (2015) 012017.
Ogunniyi "Castor oil: A vital industrial raw material" Bioresource Technology 97 (2006) 1086-1091.
Barbusinski et al., "Optimization of soapstock splitting process to reduce the concentration of impurities in wastewater" Journal of Cleaner Production 280 (2021) 124459.
Perez et al., "Organic Acids without a Carboxylic Acid Functional Group" Journal of Chemical Education • vol. 77 No. Jul. 7, 2000, p. 910-915.
De Jong et al., "Reactive Packed Bubble Column for the Synthesis of Isopropyl Myristate" Distillation Absorption 2010, p. 301-306.
Karmakar et al., "Progress and future of biodiesel synthesis: Advancements in oil extraction and conversion technologies" Energy Conversion and Management 182 (2019) 307-339.
Joelianingsih et al., "Reactivity of palm fatty acids for the non-catalytic esterification in a bubble column reactor at atmospheric pressure" Procedia Chemistry 9 ( 2014 ) 182-193.
Tan et al., "Recent Trends and Advances in Glycerol-Free Biodiesel Production" Glycerol-Free Biodiesel Production Chapter 8, p. 153-164.
Stacy et al., "Esterification of Free—Fatty—Acids to Fatty Acid Alkyl Esters in a Bubble Column Reactor for Use as Biodiesel" Fuel Processing Technology—Feb. 2014, p. 1-18.
Fiorani et al., "Dimethyl carbonate: a versatile reagent for a sustainable valorization of renewables" Green Chemistry, 2018, 20, 288-322.
Serdari et al., "Tertiary fatty amides as diesel fuel substitutes" International Journal of Energy Research, 2000; 24: 455-466.
Stacy et al., "Esterification of free fatty acids to fatty acid alkyl esters in a bubble column reactor for use as biodiesel" Fuel Processing Technology 124 (2014) 70-77.
Andreo-Martinez et al., "Production of biodiesel under supercritical conditions: State of the art and bibliometric analysis" Applied Energy 264 (2020) 114753.
Bernal et al., "Supercritical Synthesis of Biodiesel" Molecules 2012, 17, 8696-8719; doi: 10.3390/molecules17078696.
Wen et al., "Supercritical fluids technology for clean biofuel production" Progress in Natural Science 19 (2009) 273-284.
Tundo et al., "The reactions of dimethyl carbonate and its derivatives" Green Chemistry, J. Name., 2013, 00, 1-3.
Unverferth et al., "Renewable Non-Isocyanate Based Thermoplastic Polyurethanes via Polycondensation of Dimethyl Carbamate Monomers with Diols" Macromol. Rapid Commun. 2013, 34, 1569-1574.

* cited by examiner

PROCESSES FOR ORGANIC ACID ALKYL ESTER PRODUCTION USING LOW PRESSURE ALKYLATION

TECHNICAL FIELD

This invention generally relates to the economically efficient preparation of high-quality organic acid alkyl esters and co-product glycerol from feedstocks (if glycerides are present), mostly unrefined, containing a high quantity of organic acids. In alternative embodiments, the feedstocks contain a high percentage (for example, greater than about 10%) of organic acids, for example carboxylic or fatty acids. In alternative embodiments, provided are methods and industrial processes for producing an organic acid alkyl ester or esters from a feedstock containing organic acids and/or saponifiables. In alternative embodiments, the methods or industrial processes for producing organic acid alkyl esters comprise first reacting the feedstock containing organic acids with subcritical and/or supercritical alcohol, followed by transesterification with a base catalyst and alcohol, followed by purification to produce B100 biodiesel.

BACKGROUND

Biodiesel is a renewable fuel, typically a fatty acid alkyl ester, that can be blended with conventional petroleum-based diesel fuel for combustion in diesel engines. The main commercial method for producing biodiesel typically involves subjecting refined oils (for example soybean oil or palm oil) or animal fats with very low acidity (less than (<) about 2 weight percent (wt %) fatty acid) to a transesterification process in which triglycerides within the feedstock are reacted with alcohol in the presence of a basic catalyst, for example sodium hydroxide or sodium methoxide, to produce organic acid alkyl esters. Another common method that can handle higher amounts of fatty acid content involves a two-stage process wherein the feedstock is first subjected to an acid-catalyzed esterification reaction and then a second base-catalyzed transesterification reaction. While an improvement over the singular base-catalyzed method, acid/base facilities are plagued by higher capital and operating costs due to acid corrosion, heavy reagent usage and excess salt disposal. Lesser-known, unconventional methods utilize solid catalysts, enzymes or noncatalytic supercritical alcohol, and can handle up to 100% organic acid content. These unconventional methods, especially supercritical alcohol, open the door for sourcing cheaper feedstocks and allow for "greener" processing compared to conventional methods.

As stated before, conventional base-catalyzed (typically sodium methoxide, or NaOMe) biodiesel production facilities are limited in their ability to process unrefined feedstocks (free fatty acid content exceeding about 2 wt %). This limits their feedstock to refined oils, which are the most expensive on the market. NaOMe processes using refined oils cannot turn a profit anymore without government subsidies, which are never guaranteed due to ever-changing political climates. To access some of the cheaper feedstocks available (bleached fancy tallow, used cooking oil), some NaOMe facilities strip fatty acids from the high FFA feedstock to lower the acidity enough for use in the NaOMe process. This is much alternative over the glycerolysis route due to its higher operating cost and complexity. However, fatty acid strippers are typically limited to feedstocks containing less than (<) 5 wt % FFA, which excludes access to a wider range of even cheaper feedstocks with greater than 5 wt % FFA (acid oil from soapstock, distillers corn oil). Additionally, once the FFA is removed from the feedstock, it thus reduces the mass of feedstock remaining for conversion to biodiesel and creates a fatty acid byproduct stream that is usually sold at a discount to the feedstock—effectively giving away value to a third party instead of capturing that value internally by converting these fatty acids to biodiesel themselves. This feedstock limitation hinders the improvement of NaOMe process economics from achieving unquestionable sustainability/profitability, leaving NaOMe facility owners scrambling for a better solution or risk going defunct.

Adding even more to the threat of rendering NaOMe processes obsolete are an increasing amount of renewable diesel, or hydrotreated vegetable oil (HVO), facilities coming online. These facilities are typically anywhere from 10 to 50 times larger in capacity than traditional biodiesel plants and thus apply major pressure on feedstock cost and availability, effectively driving up prices across the board that squeezes smaller biodiesel players. One benefit that biodiesel facilities currently have over these HVO projects: they were here first. They are also smaller and more agile to change for a fraction of the cost of building a HVO facility.

The inventors herein propose a novel, pragmatic, retrofit solution to NaOMe biodiesel facilities that enables continued production in an ever-competitive landscape, capable of surviving without the need for government subsidy. Rather than treat the entire feedstock volume, the proposed approach targets lower volumes of high acidity (50%>) streams (stripped fatty acid, acid oil, brown grease, etc.)—effectively allowing for the acidity to be converted by a smaller, bolt-on system in comparison to the legacy NaOMe assets. This approach couples the strengths of known, first-step esterification/transesterification methods with those of conventional base catalyzed transesterification. The alternative first step—low pressure, or subcritical, alcoholysis—can typically convert more than 95% of organic acids in the feedstock into organic acid alkyl esters within 4 hours or less, without catalyst, thus leaving behind a small amount of residual organic acids and unconverted saponifiables, if present. This low acid stream can either be purified as-is or further subjected to transesterification. Combining this low acid stream with a much larger, glyceride-only stream into a base catalyzed reactor allows for neutralization of residual acidity, as well as conversion of any saponifiables, without drastically affecting the normal operation of the NaOMe process. Owner-operators with base catalysis assets find it desirable to invest a lower sum to retrofit their existing equipment (brownfield install) rather than invest a higher sum into a total greenfield installation—a commonly shared barrier to entry for newer, more environmentally friendly technologies. The art described herein provides a pragmatic hybrid approach to allow existing biodiesel players to compete in a marketplace becoming ever-crowded by renewable diesel companies.

In addition to use for biodiesel, the organic acid alkyl esters generated by the method of production outlined by this art can also be used for non-fuel purposes as well.

SUMMARY

In alternative embodiments, provided herein are methods, systems and apparatus for economically and effectively preparing an organic acid alkyl ester from a feedstock containing organic acid. In alternative embodiments, provided are methods comprising converting organic acids into organic acid alkyl esters by low pressure (for example, in alternative embodiments, low pressure is less than (<) about 20 barg, or less than about barg, or less than about 12 barg) alcoholysis and/or alkylation to generate a first reaction product mixture containing less than (<) about 5 wt % organic acid content, and apparatus for practicing these methods and processes. In alternative embodiments, generation of a first reaction product mixture is followed by purification of the first reaction product mixture to generate a purified product, or stream, containing about 95 wt % ester content or greater.

In alternative embodiments, provided are methods comprising converting organic acids contained in a feedstock into organic acid alkyl esters by low pressure (less than (<) about 20 barg) alcoholysis and/or alkylation to generate a first reaction product mixture containing less than (<) about 5 wt % organic acid content, followed by transesterification of saponifiables (such as, for example, a wax, a triacylglyceride, a glycerophospholipid or a sphingolipid or a combination thereof) in the first reaction product mixture into organic acid alkyl esters to generate a second reaction mixture containing less than (<) about 1 wt % glycerides, followed by purification of the second reaction mixture to generate a stream containing 95 wt % ester content or greater ("barg" is a unit of gauge pressure, i.e. pressure in bars above ambient or atmospheric pressure; the "g" at the end of the word "bar" (1 bar is equal to 14.5037738 psia or psig ("pounds per square inch gauge")) indicates that the measurement is not absolute pressure, which is sometimes indicated by "bara"; the key difference between psi and bar is that psi measures pressure as a one-pound force applied on an area of one square inch whereas bar measures pressure as a force applied perpendicularly on a unit area of a surface; and specifically, psi measures pressure or stress, whereas bar only measures pressure); and apparatus for practicing these methods.

In alternative embodiments, provided are methods comprising converting organic acids into organic acid alkyl esters, followed by purification to 95 wt % ester content or greater; and apparatus for practicing these methods.

In alternative embodiments, provided are industrial processes for producing an organic acid alky ester from a feedstock containing organic acids and/or saponifiables, comprising: countercurrently contacting a feedstock with an organic alkylating reagent over two or more vessels or stages at temperature between 100° C. and 400° C. and pressure between 0.1 barg and 355 barg while simultaneously removing water and/or glycerin with unreacted alkylating reagent from the final vessel or stage to result in a first reaction method product containing organic acid alkyl esters, followed by a choice of using the alkyl esters as-is, purifying the organic acid alkyl esters from the first reaction product mixture or subjecting the first reaction product mixture to an additional transesterification reaction to convert saponifiables into additional organic acid alkyl esters, then purifying the organic acid alkyl esters from this second reaction method product.

In alternative embodiments, provided are methods or processes, or a first reaction method or an industrial process, for producing an organic acid alkyl ester comprising:
  conducting an esterification reaction between:
    (i) a feedstock comprising an organic acid; and,
    (ii) an alkylating reagent, with or without catalyst,
  wherein the esterification reaction conditions comprise a temperature of between about 100° C. to 400° C. and a pressure of between about 0.1 barg to 355 barg, to generate a first reaction method or process product,
    optionally reacting for between about 1 second and 72 hours, or 1 minute and 48 hours, or 5 minutes and 25 hours,
  wherein the alkylating reagent comprises one or multiple alkylating compounds or reagents,
  wherein the one or multiple alkylating compounds or reagents comprises: a monohydric alcohol, a polyhydric alcohol, an alkyl carbonate, an alkyl sulfate, an alkyl ether, an alkyl sulfate, an alkyl halide, an alkyl ester or a combination thereof, and
  wherein the minimum amount of organic acid contained in the feedstock is about parts per million (ppm), or between about 45 to 55 ppm, or between about 40 to 60 ppm.

In alternative embodiments of methods and processes, or industrial processes, as provided herein:
  the methods or processes, or industrial processes, further comprise desolventizing and/or neutralizing the first reaction method or process product to generate desolventized and/or neutralized first reaction method or process products (also called derivatives of the first reaction method or process product);
  the alkyl chain or the alkylating reagent comprises 1, 2, 3, 4, 5 or 6 carbons: or, the alkyl carbonate, alkyl sulfate, alkyl ether, alkyl sulfate, alkyl halide or alkyl ester comprises a methyl carbonate, methyl sulfate, methyl ether, methyl sulfate, methyl halide or methyl ester, respectively; or an ethyl carbonate, an ethyl sulfate, an ethyl ether, an ethyl sulfate, an ethyl halide or an ethyl ester, respectively;
  the catalyst, if present, comprises: (a) an organic or an inorganic catalyst; or (b) a heterogeneous acid catalyst that is insoluble in a reaction medium;
  the catalyst, if present, comprises a liquid metal catalyst that is soluble in a reaction medium, and optionally the liquid metal catalyst comprises one or more metal salts of an organic acid of any valence, and optionally the metal comprises any metal capable of creating a positive counterion to an organic acid;
  the feedstock comprises greater than about 10%, or between about 5% to 10%, or between about 2% to 20%, of one or multiple organic acids;
  the organic acid comprises one or a multiple of carboxylic acids or fatty acids;
  the feedstock comprises one or multiple organic acids and/or one or multiple saponifiable compounds, and optionally the one or multiple saponifiable compounds comprises a wax, a triacylglyceride, a diglyceride, a monoglyceride, a glycerophospholipid or a sphingolipid or a combination thereof;
  the feedstock comprises:
    a soft seed acid oil, optionally originating from a direct acidulation of a soft seed soapstock;
    a brown grease, optionally originating from a fat, oil or grease (FOG) effluent;
    a Soap Carbonate Technology (SCT) product, and optionally the SCT product comprises one or a plurality of organic acids gererated by thermal hydrolysis or saponification of soapstock, followed by acidulation with optional purification; and/or
    an organic acid, or an organic acid and alkyl ester mixture, optionally originating from acidulation of glycerin separated from base catalytic transesterification reaction mixtures; and/or
  the alcohol comprises an alcohol having between 1 and 5 carbons, or 1, 2, 3, 4, 6, 7 or 8 or more carbons, or the alcohol comprises: methanol, ethanol, propanol, butanol, isobutanol, isopropyl alcohol or a combination thereof.

In alternative embodiments, provided are methods or processes, or an industrial process, for producing an organic acid alkyl ester from a feedstock comprising about 50 weight percent (wt %) or less, or between about 50 wt % and 5 wt %, or between about 50 wt % and 50 ppm, organic acid, with or without a catalyst, comprising:

(a) steam or gas stripping the feedstock to generate:
  (i) a first stream (a so-called "stripper lights" stream) comprising about 50 wt % or more organic acid content; and,
  (ii) a second stream (a so-called "stripper heavies" stream) comprising about 5 wt % or less organic acid content,
(b) separating the first stream and the second stream under conditions that separate the first stream from the second stream, wherein optionally the separating conditions comprise atmospheric pressure or vacuum pressure at a temperature of between about 150° C. to 280° C., while feeding nitrogen or steam into feedstock or material being stripped, and then separately reacting the separated streams:
  (i) first stream using a first reaction process to reduce the acid value to less than 20, or optionally to less than 5, to generate a first reaction process product; and,
  (ii) second stream using a second reaction process to generate a second reaction process product with glyceride content of about 5 wt % or less, or optionally to about 1 wt % or less,
(c) combining the first reaction process product into the second reaction process at any point to neutralize any unreacted or residual organic acids and to convert any unreacted or remaining glycerides into organic acid alkyl esters via the second reaction process, thus adding to the mass of the second reaction process product, wherein the second reaction process optionally utilizes two transesterification reactors and three decanters.

In alternative embodiments, provided are apparatus or systems, or industrial systems, or products of manufacture, for preparing an organic acid alkyl ester from a feedstock comprising an organic acid and one or a plurality of saponifiable compounds, the apparatus or system comprising a first reactor or stage, a second reactor or stage and a third reactor or stage, wherein the first reactor or stage is operatively connected to the second reactor or stage, and the second reactor or stage is operatively connected to the third reactor or stage, wherein the first reactor or stage is configured for operating under conditions comprising a temperature of between about 100° C. to 400° C. and pressure of between about 0.1 barg to 355 barg, for esterifying and/or transesterifying the feedstock containing organic acid with no more than about 10:1 alkylating reagent by mass ratio about the feedstock, the alkylating agent being fed for up to about 72 hours, or between about 10 and 80 hours, and comprising up to 5 wt % moisture, or between about 1 wt % and 10 wt % moisture, originating from the second reactor, with or without catalyst, to reduce the acid value to about 100 or less, or optionally to an acid value of 90, 80, 70, 60, 50, 40 or 35 or less, thereby generating the organic acid alkyl ester, which is fed into the next, or second reactor or stage; and wherein the second reactor or stage is configured for operating under conditions comprising at least about 0.1 barg above the first reactor or stage for further reducing the acid value of the organic acid alkyl ester fed in from the first reactor to about 40 or less, or optionally reducing to an acid value of about 10 or less, or reducing to an acid value of between about 1 and 10, by utilizing or feeding into the reactor excess alkylating reagent, or a molar excess of alkylating reagent as compared to organic acid alkyl ester, containing up to 1 wt % moisture, or between about 0.5 wt % and 5 wt % moisture, originating or fed in from the third reactor, thus generating additional organic acid alkyl ester, which is fed into the next, or the third reactor or stage; and a third reactor or stage configured for generating and operating under conditions comprising least 0.1 barg in pressure above the second reactor or stage for further reducing the acid value of the organic acid alkyl ester fed in from the second reactor or stage to about 20 or less, or reducing to an acid value of 18, 15, 12, 10, 8, 5 or 2 or less, by utilizing excess alkylating reagent, or a molar excess of alkylating reagent as compared to organic acid alkyl ester, that has been separated from water that originates from the first reactor or stage, wherein apparatus is configured such that the feedstock and organic acid alkyl ester flows from the first reactor or stage to the second reactor or stage to the third reactor or stage;

wherein apparatus is configured such that the alkylating reagent can flow from third reactor or stage to the second reactor or stage to the first reactor or stage, wherein the alkylating reagent is purified or substantially purified to remove water, and optionally between about 90% to 99.5% of the water is removed, then the alkylating reagent is combined with fresh makeup alkylating reagent to flow back to third reactor or stage, wherein optionally the alkylating reagent is separated from water by a process comprising distillation, use of molecular sieve or a combination thereof, thereby generating a first reaction method or process product comprising an organic acid alkyl ester with an acid value of at least 20 or less, or having an acid value of between about 0.5 and 20.

In alternative embodiments of the apparatus or systems as provided herein:

the apparatus or systems are configured to desolventize and/or neutralize the first reaction method or process product to generate desolventized and/or neutralized first reaction method or process products (also called derivatives of the first reaction method or process product);

the apparatus or systems are configured for subjecting the first reaction method or process product or any of its derivatives to a second reaction process comprising a transesterification reaction to convert at least about 5%, 10%, 15%, 20% or 25% of the unreacted or remaining saponifiables contained in the first reaction process product into organic acid alkyl esters, wherein the second reaction process comprises a transesterification reaction comprising use of a catalyst, optionally having 10% wt % or less catalyst or enzyme in relation to material being reacted, or having between about 1% wt % and 15 wt % catalyst or enzyme in relation to material being reacted, and about 10:1 mass ratio or less alcohol in relation to material being reacted, under reaction conditions comprising 1 sec to 24 hrs reaction time per reactor, or 1 hour to 10 hrs reaction time per reactor, and at a 20° C. to 300° C. temp, and 0 to about 355 barg pressure, and optionally the second reaction process further comprises separating the reaction product, optionally using centrifugation and/or decantation, and optionally the decantation is under conditions comprising: 100° C. or less, or between 90° C. and 35° C. about, for up to 8 hrs, or between about 1 to 12 hours;

the apparatus or systems comprise at least a first pressurized vessel configured for an capable of generating concurrent or countercurrent reaction stages wherein a first reaction method or process is conducted in, and wherein the first reaction process in the first pressurized vessel generates the highest acid value of materials contained within the apparatus, wherein the contact time in the first pressurized vessel between a feedstock containing organic acid and the alkylating reagent is between about 0.1 to 24 hours, wherein the reacted material containing organic acid and/or organic acid alkyl ester located in the final pressurized vessel or stage is contacted with alkylating reagent containing the least amount of water so as to push the acid value to the desired level, wherein the acid value of the first reaction method product is less than 5 percent of the feedstock entering the first vessel or stage, wherein the first reaction method or process comprises conducting an esterification reaction between: (i) a feedstock comprising an organic acid; and, (ii) an alkylating reagent, with or without catalyst, wherein the esterification reaction conditions comprise a temperature of between about 100° C. to 400° C. and a pressure of between about 0.1 barg to 355 barg, to generate a first reaction method or process product, optionally reacting for between about 1 second and 72 hours, or 1 minute and 48 hours, or 5 minutes and 25 hours, wherein the alkylating reagent comprises one or multiple alkylating compounds or reagents, wherein the one or multiple alkylating compounds or reagents comprises: a monohydric alcohol, a polyhydric alcohol, an alkyl carbonate, an alkyl sulfate, an alkyl ether, an alkyl sulfate, an alkyl halide, an alkyl ester or a combination thereof, and wherein the minimum amount of organic acid contained in the feedstock is about parts per million (ppm), or between about 45 to 55 ppm, or between about 40 to 60 ppm.

the apparatus or systems comprise one or more pressurized vessels or stages configured as a countercurrent reactor system and/or sequence, with countercurrent usage of an alkylating reagent to conduct or carry out the first reaction process, wherein a feedstock containing organic acid inside a first pressurized vessel or stage is contacted by a vaporized alkylating reagent containing at least a portion of water originating from at least one of the pressurized vessels or stages located further along the countercurrent reactor system and/or sequence, the first reaction process product or any of its derivatives is subjected to a second reaction process comprising a transesterification reaction to convert at least about 5%, 10%, 15%, 20% or 25% of the unreacted or remaining saponifiables contained in the first reaction process product into organic acid alkyl esters; and/or the feedstock containing organic acids also comprises one or more saponifiable compounds, and optionally the one or more saponifiable compound comprises a glyceride or a natural wax, wherein optionally at least a portion of the one or more saponifiable compounds are converted to organic acid alkyl esters via transesterification, and at least a portion of the glycerin formed during the transesterification is removed with excess alkylating reagent in a vapor phase.

In alternative embodiments, methods or industrial processes as provided herein further comprise subjecting (or the apparatus as provided herein are configured to subject) the first reaction process product to one or more purification processes to generate an organic acid alkyl ester stream of about 95 weight percent (wt %) or greater, or between about 80 wt % and 99 wt %, wherein optionally, the first reaction process product is sufficiently low in residual organic acids, or has less that about 1 wt % organic acids, or has between about wt % and 2 wt % organic acids, such that it can be purified by distillation to generate organic acid alkyl esters that meet B100 specifications.

In alternative embodiments of methods or industrial processes as provided herein, the first reaction method product or any of its derivatives is subjected to (or the apparatus as provided herein are configured to carry out) a second reaction method comprising a transesterification reaction to convert at least a portion of (or at least between about 1% to 50% of, or between about 5% and 20% of) the remaining saponifiables contained in the first reaction method product into organic acid alkyl esters, wherein optionally, the transesterification reaction is catalyzed by an acid or base and utilizes one or more alcohols as reactant, and wherein any residual organic acid content in the first reaction method product or any of its derivatives is neutralized by the same base catalyst used during transesterification if a base catalyst is used.

In alternative embodiments of methods or industrial processes as provided herein (or the apparatus as provided herein are configured to comprise) at least one pressurized vessel or stage utilizes a pumparound pressure loop that operates at higher pressure than the pressurized vessel or stage, wherein the esterification reaction rate within the pumparound pressure loop is higher than within the pressurized vessel or stage, wherein the relative volume of the pumparound pressure loop is less than or equal to about 20%, or less than or equal to about 10% and 50%, of the pressurized vessel or stage volume, wherein the relative pressure of the pumparound pressure loop is at least about 2% greater, or at least between about 0.5% and 5% greater, than the operating pressure of the pressurized vessel or stage but no more than about 1200% or between about 1000% and 1400%, wherein optionally the pumparound pressure loop utilizes hydrodynamic cavitation to intensify reaction kinetics, wherein optionally at least a portion of (or between about 1% and 50% of, or between about 5% and 20% of) the alkylating reagent is introduced into the pumparound pressure loop to increase reaction kinetics due to a higher molar ratio of organic reagent to saponifiable content, wherein optionally the alkylating reagent is at or above its critical point, and optionally the critical point is about 239° C. and 81.1 barg for methanol.

In alternative embodiments of methods or industrial processes as provided herein (or the apparatus as provided herein are configured to generate) at least a portion of the feedstock comprises a mixture of organic acid and organic acid alkyl ester isolated from glycerin that originates from the second reaction process.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of embodiments as provided herein and are not meant to limit the scope of the invention as encompassed by the claims.

Like reference symbols in the various drawings indicate like elements.

Figure 1:
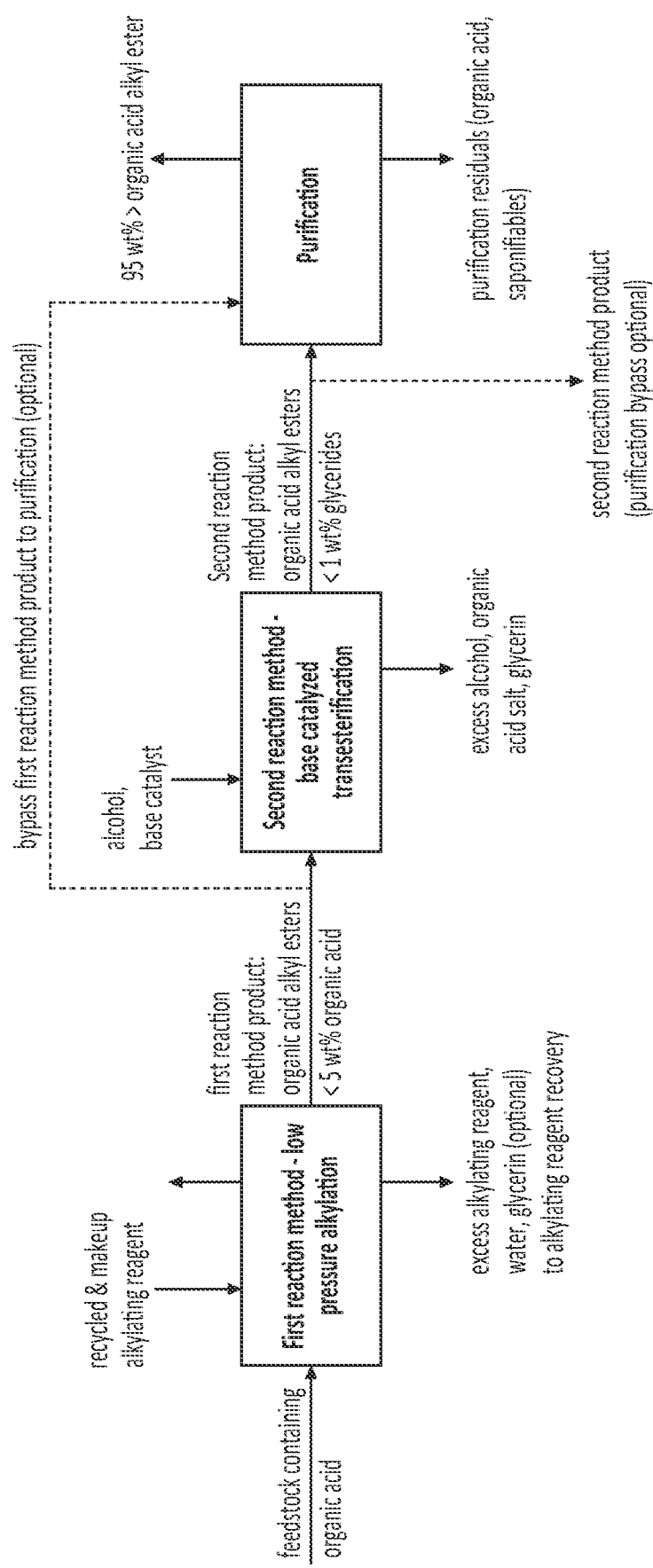
FIG. 1 illustrates an exemplary apparatus for carrying out an exemplary method as provided herein for preparing organic acid alkyl esters.
Figure 2:
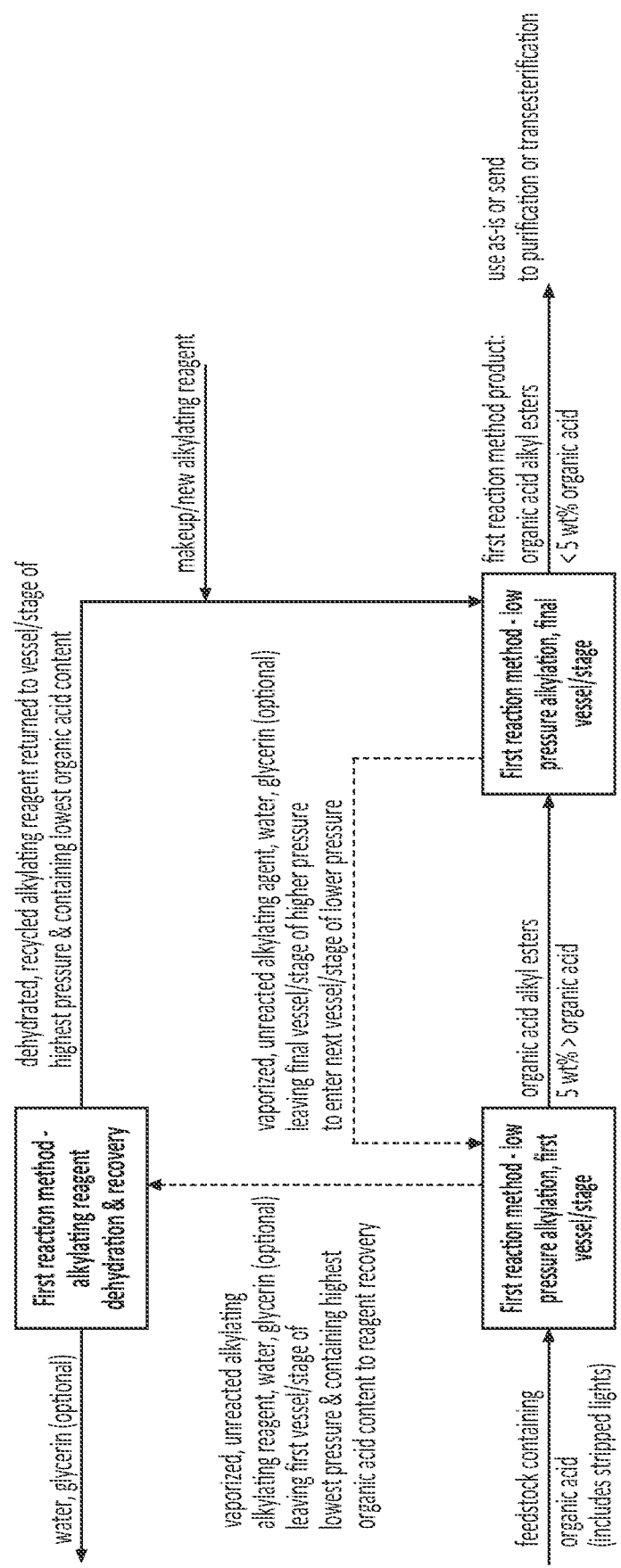
FIG. 2 illustrates a diagram showing part of a configuration of an exemplary apparatus for carrying out an exemplary method as provided herein for preparing organic acid alkyl esters.
Figure 3:
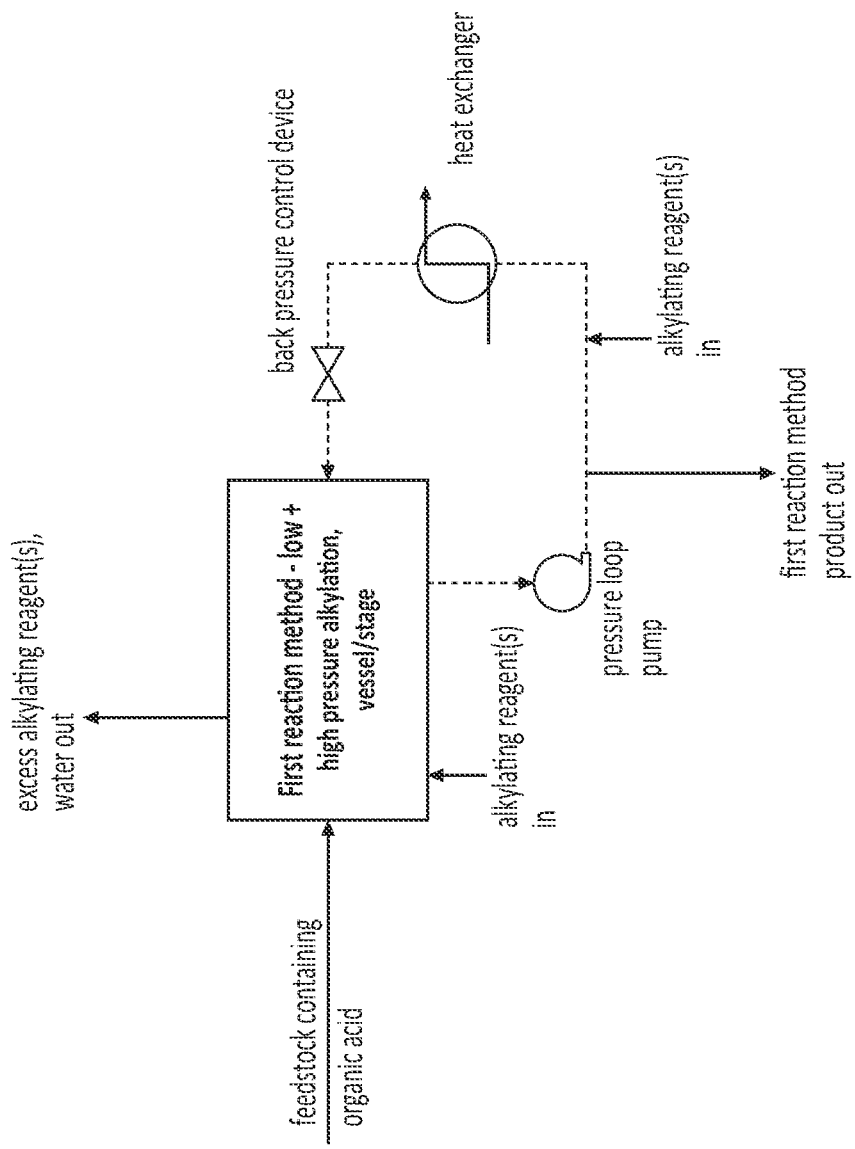
FIG. 3 illustrates a diagram showing part of a configuration of an exemplary apparatus for carrying out an exemplary method as provided herein for preparing organic acid alkyl esters.
Figure 4:
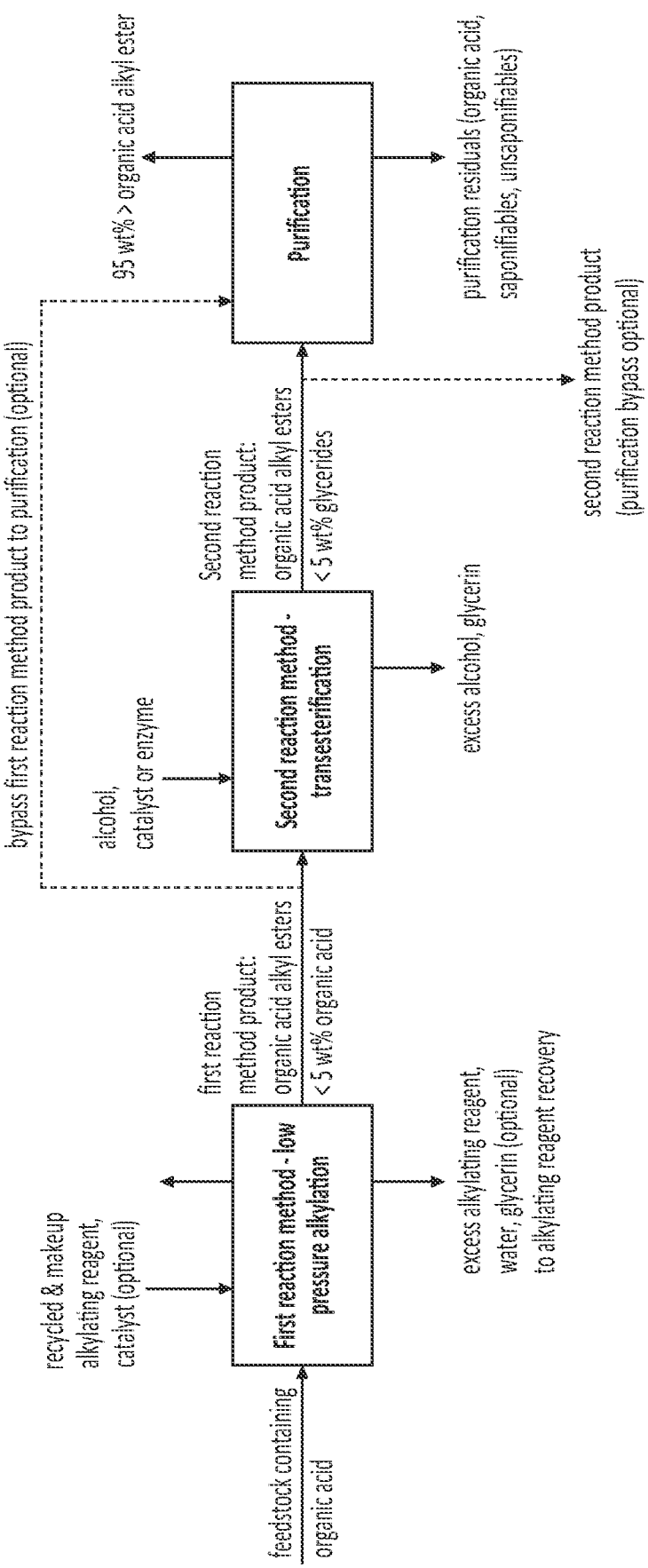
FIG. 4 illustrates a diagram showing the entire configuration of an exemplary apparatus for carrying out an exemplary method as provided herein for preparing organic acid alkyl esters.

Reference will now be made in detail to various exemplary embodiments, examples of which are illustrated in the accompanying drawings. The following detailed description is provided to give the reader a better understanding of certain details of aspects and embodiments as provided herein, and should not be interpreted as a limitation on the scope of the invention.

DETAILED DESCRIPTION

In alternative embodiments, provided are apparatus, systems and processes for the economically efficient preparation of long-chain fatty acid esters (FAEs), or high-quality biodiesel, and optionally other products from feedstocks containing organic acids.

In alternative embodiments, systems and processes as provided herein comprise one or more reactions comprising mixing the natural oil and/or mixed lipid feedstock with an alcohol and driving the reaction using temperature and pressure alone, i.e. without the use of any catalyst, the use of which is the standard in the art for producing biodiesel products from feedstocks containing organic acids. In alternative embodiments, the systems and processes as provided herein are more economical and efficient than currently used approaches for the generation of biodiesel from feedstocks containing organic acids.

In alternative embodiments, the feedstock containing organic acids, including the natural oils and/or mixed lipid feedstocks used to practice the methods and processes provided herein, is comprised of lipids derived from (for example, isolated from) or equivalent to: a natural source, for example, a bacterial, algae, kelp, plant or an animal source, or a bioengineered source.

In alternative embodiments, a feedstock containing organic acids is subjected to a first reaction method or process utilizing alkylating reagent that is conducted at a temperature of between 100° C. to 400° C. and pressure between 0.1 to 350 barg for 1 second to 48 hours (or between about 1 minute to 24 hours, or 5 minutes to 12 hours) in one, or two or more vessels or stages, to yield a first reaction method or process product mixture with an acid value (AV) of less than (<) about 30, or having an AV of between about 25 to 35.

In alternative embodiments, a feedstock containing organic acids is subjected to a first reaction method or process utilizing alkylating reagent that is conducted at a temperature between about 180° C. to 300° C. and pressure of between about 11.7 to 40 barg for between 1 to 24 hours (or between about 30 minutes to 12 hours) in two or more vessels or stages to yield a first reaction product mixture with an AV of less than (<) about 12, or an AV of less than about 15 or 10, or an AV of between about 2 to 10 or 1 to 5.

In alternative embodiments, the alkylating reagent utilized comprises one or more of the following: alcohol, alkyl carbonate, alkyl ether, alkyl sulfate, alkyl halide. In alternative embodiments the alkylating reagent comprises at least one alcohol. Water scavenging reagents, such as anhydrides, may also be used to push the esterification equilibrium forward.

In alternative embodiments, water, organic acids and/or organic acid salts is or are added to the first reaction method or process and/or first reaction method product. In alternative embodiments acidified organic acid salts recovered from downstream neutralization operations are recycled to the first reaction method. If amine salts of organic acids are fed to the first reaction method, then at least a portion (or between about 5% to 50%) are converted organic acid amides. In alternative embodiments, at least about 90%, or between about 80% and 95%, or between about 70% and 98%, of organic acid content entering the first reaction method is converted to organic acid alkyl esters.

In alternative embodiments, a feedstock containing organic acids is subjected to a first reaction method or process utilizing three or more stages or vessels in series that operate in descending pressures that allow for countercurrent flow of alkylating reagent vapor from a higher pressure stage or vessel to a lower pressure stage or vessel. In alternative embodiments, a "stage" is defined as a certain time window at a specific temperature and pressure in which the acid value (AV) of the material is reduced, for example, is reduced from an A to B value.

As used herein, "acid value" (AV) (or neutralization number or acid number or acidity) is the mass of potassium hydroxide (KOH) in milligrams that is required to neutralize one gram of chemical substance. The acid number is a measure of the number of carboxylic acid groups in a chemical compound, such as a fatty acid, or in a mixture of compounds. In an exemplary procedure to determine AV, a known amount of sample dissolved in an organic solvent (often isopropanol) and titrated with a solution of alcoholic potassium hydroxide (KOH) of known concentration using phenolphthalein as a color indicator.

For example, in alternative embodiments, in a system of three vessels there are three main "stages" that the feedstock moves through: filling, reacting, emptying. Each stage or vessel can operate between 0.1 to 24 hours (hrs), alternatively or optionally between 3 to 8 hrs. Each stage may occur in one vessel or across multiple vessels. In alternative embodiments, the first stage reduces the acid value (AV) of the feedstock by 80% or more, or by 90% or more, or the first stage reduces the AV between about 75% and 98%.

In alternative embodiments, each additional stage reduces the acid value (AV) of the material by about 30% or more, or by between about 20% to 50%, or alternatively or optionally by 50% or more, or by between about 50% to 90%.

In alternative embodiments, feedstock is loaded into the first stage or vessel, or "filling" stage or vessel, brought to reaction temperature and contacted with excess (for example, a molar excess of) wet alkylating reagent vapor originating from the "reacting" stage or vessel. In alternative embodiments loading, heating and contact with alkylating reagent occurs sequentially, or occurs in parallel so as to minimize residence time of the material in any certain stage or vessel.

In alternative embodiments, the filling stage or vessel operates at the lowest pressure in relation to the stages or vessel downstream, which allows for proper transfer of alkylating reagent vapor from one stage or vessel to the next. In alternative embodiments, the filling stage or vessel also operates at the lowest temperature in relation to the downstream stages or vessels, which allows for higher solubility of the alkylating reagent to maximize the push forward of the esterification and/or transesterification reaction equilibrium. In alternative embodiments, the further the acid value (AV) is reduced in the filling stage or vessel, the more moisture can be removed after esterification and the less moisture content will be contained in the alkylating reagent that is accepted from the reacting stage or vessel.

In alternative embodiments, once the material completes its residence time within the filling stage/vessel; optionally having an acid value (AV) of about 35 or less, or alternatively or optionally about 10 or less, or having an AV of between about 40 and 4; it then moves on to the "reacting" stage or vessel.

In alternative embodiments, the reacting stage or vessel operates at higher temperature and pressure than the filling stage, as well as 1.5 to 2.5 times the residence time of the filling stage. In alternative embodiments, the role of the reacting stage or vessel is to reduce the acid value (AV) to less than 5, or optionally less than about 2, or to between about 10 and 1, by the end of the residence time.

In alternative embodiments, this sets up the final stage, the "emptying" stage, to reduce the acid value to less than about 1, or optionally less than about 0.5, or to an AV of between about 2 and 0.25.

In alternative embodiments, once the material completes its residence time in the reacting stage/vessel, it then moves to the emptying stage/vessel, which can operate at a higher pressure, and/or a similar temperature, and at between about 25% to 75% the residence time of that of the reacting stage or vessel.

In alternative embodiments a countercurrent system is used, and the emptying stage or vessel accepts the driest alkylating reagent. This allows for a maximal push of reaction equilibria to meet the acid value target of about 1 or less (or between about 2 and by the end of the emptying stage or vessel residence time.

In alternative embodiments, the alkylating reagent is methanol.

In alternative embodiments, the alkylating reagent is fed to the third stage or vessel (highest pressure relative to the first and second state or vessels) to contact material that has already been subjected to first reaction method conditions in the previous two stages or vessels to greatly reduce the acid value (AV) of the material, optionally reducing AV by greater than about 90%, or reducing AV between about 75% to 99%, of the original feedstock acid value (AV) by the time the material reaches the third stage or vessel.

In alternative embodiments, the alkylating reagent contacting the third stage or vessel contains the least amount of moisture, and can be either virgin, recycled from a moisture-removing separator (for example distillation column), or a combination of virgin and recycled. In alternative embodiments, the material leaving the third stage/vessel, or the "emptying" vessel, also referred to as the "first reaction method product", can have an acid value (AV) of about 2% or less, or between about 1% and 10%, of the acid value (AV) of the feedstock initially loaded into the filling stage/vessel.

In alternative embodiments, the first reaction product mixture is combined with an organic and/or inorganic basic reagent to reduce the AV to less than (<) about 0.2, or to between about 0.4 and 0.05, thus resulting in a neutralized or substantially neutralized lipid phase. In alternative embodiments, the first reaction product mixture is cooled to as low as room temperature (RT) or ambient temperature prior to combination with basic reagent.

In alternative embodiments, the basic reagent utilized is comprised of any oxide, alkoxide, hydroxide, carbonate, bicarbonate, ammonia, any amine or amine derivative, or any combination thereof. In alternative embodiments the basic reagent comprises a monovalent hydroxide and/or alkoxide that is very soluble in water and/or alcohol and quick to react with organic acids to form monovalent organic acid salts. In alternative embodiments, the basic reagent is sourced from recycled base catalyst from the second reaction method, where the recycled base catalyst may contains some (for example, 0.1 to %) glycerin. The exemplary approach of using the glycerin containing basic catalyst to neutralize the first reaction method product allows for savings in operating cost in at least two main ways:

avoidance of neutralizing the base catalyst (for example sodium methoxide) with inorganic acid (for example hydrochloric acid) after the second reaction method and, avoidance of purchasing a separate basic reagent (for example sodium hydroxide) for neutralizing the lipid phase originating from the first reaction method.

In alternative embodiments, by essentially double (or repeat) using the base catalyst to neutralize AV in the lipid phase from the first reaction method, less salt (for example sodium chloride) is produced when the organic acid salts are acidulated. In alternative embodiments, after organic acid salts are formed, they are removed (or substantially removed, or between about 90% to 99% removed) from the neutralized lipid phase and/or remain with the neutralized lipid phase.

In alternative embodiments, the first reaction product mixture produced contains an acid value (AV) in excess of the B100 specification for biodiesel and must undergo a neutralization step, for example, either by chemical or adsorptive means, that reduces the acid value to meet the B100 specification (according to the American Society for Testing and Materials (ASTM), biodiesel B100 is defined as a fuel comprised of mono-alkyl (methyl) esters of long chain fatty acids derived from vegetable oils or animal fats, and meeting the requirements of ASTM D 6751; for biodiesel to be sold in the market, the fuel must meet certain quality specifications; in the United States, biodiesel must meet the American Society for Testing and Materials (ASTM) requirements for biodiesel fuel in its D 6751 standard, and the standard in Europe is defined by EN14214).

In alternative embodiments, because the acid value (AV) of the first reaction product mixture produced contains an acid value (AV) up to about 2 (or between about and 4), it is then subjected to a neutralization step, for example, either by chemical or adsorptive means, that reduces the acid value to less than about 0.5, or less than 0.3, or to between about 0.1 to 1.

In alternative embodiments, the alcohol used in a reaction or a process as provided herein contains one or multiple alcohols that are between 1 and 5 carbons, or 1, 2, 3, 4, 5, 6, 7 or 8 or more carbons, for example methanol, ethanol, propanol, butanol, isobutanol, isopropyl alcohol or a combination thereof. In various other embodiments, conditions may be such that a higher alcohol containing more than 5, 6, 7 or 8 or more carbons are used.

In alternative embodiments, or the methods or industrial processes as provided herein, the purification residuals comprise organic acid alkyl esters, unreacted Free Fatty Acids (FFAs), any unreacted esters for example mono- di- and triglycerides, phospholipids, and any other unsaponifiable material in the feedstock, optionally sterols, vitamin E compounds (tocopherols and/or tocotrienols), squalene, or other compounds.

In alternative embodiments, the methods or industrial processes as provided herein further comprise subjecting the purification residuals to downstream separation to valorize (or recycle) the components into higher value components or fractions. Examples of downstream separation methods or industrial processes used on the distillation bottoms include, but are not limited to: short path distillation, molecular distillation, crystallization, saponification/acidulation, liquid/liquid extraction, and the like, and examples of higher value fractions or components include, but are not limited to: oryzanol, sterols, sterol esters, tocopherols, squalene, terpene, and the like.

In alternative embodiments, the methods or industrial processes as provided herein further comprise processing the second reaction product mixture to separate the organic acid alkyl esters from the remaining components of the product mixture, optionally by distilling to generate an organic acid alkyl ester product that is suitable for use as an ASTM B100 biodiesel.

In alternative embodiments, methods or industrial processes as provided herein (or the apparatus as provided herein are configured to) further comprise a step of subjecting the first reaction product or any of its derivatives to a chemical neutralization and separation step to reduce the acid value (AV) to meet the B100 specification for biodiesel if it does not already meet the B100 specification, wherein optionally, chemical neutralization is conducted with one or more hydroxides, carbonates, oxides, bicarbonates, amines, or any combination thereof, and optionally, chemical neutralization is aided by the addition of up to about 10% volume of water, or up to between about 5% to 15% or between about 1% and 25% volume of water, with respect to the fatty acid alkyl ester, and optionally, after the chemical neutralization step has been concluded, the neutralized mixture is subjected to a separation step that comprises centrifugation, decantation, filtration, or any combination thereof, thereby producing a neutralized organic acid alkyl ester that can meet, or substantially meet, the B100 specification for biodiesel.

In alternative embodiments, the neutralization of organic acid via base is conducted with an alkaline reagent comprising any oxide, alkoxide, hydroxide, carbonate, bicarbonate, amine, ion exchange resin, or equivalents, or any combination thereof.

In alternative embodiments, the neutralization of organic acid via base produces an organic acid salt that is removed (or substantially removed, or 90% to 99% of the organic acid salt is removed) from the organic acid alkyl ester by one or multiple methods comprising filtration, centrifugation, washing, adsorption, ion exchange, or equivalents, or any combination thereof.

In alternative embodiments, the organic acid salt removed from the organic acid alkyl ester comprises sodium, potassium, calcium, magnesium, iron, aluminum, or any combination thereof, wherein optionally, the organic acid salt removed from the organic acid alkyl ester comprises entrained organic acid alkyl ester, and optionally, the entrained organic acid alkyl ester can be recovered by one or multiple steps comprising washing, evaporation, solid-liquid extraction, acidulation or equivalents.

In alternative embodiments, a system (for example, for practicing methods or industrial processes as provided herein) is provided for converting natural oil and/or mixed lipid feedstocks into high-quality biodiesel without the use of any catalysts based on the composition of the natural oil feedstock used in the system. In alternative embodiments, the system is comprised of multiple operational units that are configured in alternative arrangements to accommodate the composition of the feedstock that is being converted to biodiesel and optionally other products.

In alternative embodiments, a system as provided herein is "feedstock flexible", meaning that the system is configured to process natural oils and/or mixed lipid feedstocks with any free fatty acid content (for example, including any ratio of esters, for example glycerides, to free fatty acid) to and any fatty acid profile (for example percent saturated and unsaturated fatty acids). This exemplary embodiment provides a significant improvement over prior approaches to converting natural oil feedstocks and/or mixed lipid feedstocks to biodiesel in which systems are configured to handle a narrow range of feedstocks and are limited in their ability to process feedstocks comprising high free fatty acid (FFA) content, for example feedstocks with greater than 10% FFA, or feedstocks with between about 5% and 50% FFA.

In alternative embodiments, a system is provided that replaces conventional fatty acid methyl ester production from lauric oils, for example, coconut oil and/or palm kernel oil. In alternative embodiments, this is useful in the formation of oleochemical (or any fat or oil) building blocks.

In alternative embodiments, a catalyst or enzyme may be used to aid in the esterification and/or transesterification (for example, alcoholysis) of the feedstock.

In alternative embodiments, the systems and processes provided herein are used to isolate compounds with low or no volatility, for example, sterol esters, oryzanol, tocopherols, squalene, and the like. In one embodiment, organic acid alkyl esters are first formed by the systems and processes described, then separated from the low volatility components by distillation or other means. This is a useful approach for the isolation of specialty and fine chemical compounds.

In alternative embodiments, organic acid alkyl esters are recovered from the second reaction product mixture via evaporative measures following a drying and/or desolventizing section, for example, by distillation with stripping and rectification sections.

In alternative embodiments, hydrodynamic cavitation may be used in one or multiple locations of the methods and/or industrial processes described. This helps to intensify the process by creating a large pressure drop across a relatively small area. In alternative embodiments, this reduces process parameter intensity, including temperature and residence time, resulting in lower capital and operating costs.

In alternative embodiments, reactive distillation is utilized in one or multiple locations of the methods and/or industrial processes described. Reactive distillation helps to push equilibrium toward higher formation of products, which can be useful in optimizing conventional reactor and distillation systems to achieve more desirable results.

In alternative embodiments, organic acid alkyl esters (that are separated from other saponifiables (such as, for example, a wax, a triacylglyceride, a diglyceride, a monoglyceride, a glycerophospholipid or a sphingolipid or a combination thereof) and/or unsaponifiables) can be contaminated with organic acids, for example fatty acids. In alternative embodiments, for B100 biodiesel, it is desirable to have a low acid value specification before the fuel is sold. To reach this specification, any method known in the art may be used to reduce and/or remove the organic acid, for example fatty acid, contaminants from the fatty acid alkyl ester stream. In alternative embodiments, these methods include, but are not limited to: distillation, neutralization with base, adsorption/absorption with a solid phase, liquid-liquid extraction, crystallization, or any combination thereof, and the like.

Feedstock Origin

In alternative embodiments, the feedstock containing organic acid is a smaller byproduct stream rich in organic acids that originates from a larger stream that is rich in glycerides. In alternative embodiments, the feedstock containing organic acid is a steam or gas stripped distillate that is much higher in organic acid content and much lower in glyceride content than the original feedstock entering the feedstock stripper. The original feedstock entering the stripper typically contains anywhere from between about 0 to 20 wt %, or optionally 1% to 15 wt % or 2% to 30 wt %, organic acids.

In alternative embodiments, the stripper reduces organic acid content of the original feedstock to less than about 0.5 wt %, or optionally to less than about 0.1 wt %, to between about 0.05 wt % and 1 wt % organic acid, to create a feedstock deficient in organic acids that is ideal for base catalyzed transesterification, or "second reaction method".

In alternative embodiments, the stripped distillate, optionally 50 wt % or more, or between about 40% and 90%, of organic acid content, is ideal for vapor phase esterification/transesterification by alkylating reagent (with or without catalyst, alternatively or optionally without), or "first reaction method".

In alternative embodiments, the feedstock containing organic acids originates from source other than a steam or gas stripper. The feedstock containing organic acids can be sourced and fed directly to the first reaction method. In alternative embodiments, these feedstocks are above the design limit of the stripper (for example, above 20 wt % or wt % organic acid content), so they are typically not good candidates for stripping to generate the typical organic acid-heavy and glyceride-heavy streams that are divided between the first and second reaction methods. In alternative embodiments, these "in-between" feedstocks contain between about 20% and 100% organic acid content, or optionally between 50% to 100 wt % organic acid content. Examples of these "in-between" feedstocks include soft seed acid oil (originating from direct acidulation of soft seed soapstock), brown grease (originating from fat/oil/grease effluents, or FOG) or alternatives such as Soap Carbonate Technology products (heavy in organic acids that are created by thermal hydrolysis or saponification of soapstock, followed by acidulation with optional purification) and organic acid/organic acid alkyl ester mixtures (alternatively or optionally originating from acidulation of glycerin separated from base catalytic transesterification reaction mixtures).

In alternative embodiments, organic acid alkyl esters produced by enzymatic transesterification as provided herein, which can be generated using an immobilized lipase enzyme such as for example NOVOZYM 435™ (Novozyme, Copenhagen, Denmark); and in alternative embodiments the organic acid alkyl esters so produced can contain up to 5 wt % residual organic acids (or between 1 wt % and 10 wt %), and in alternative embodiments the residual organic acids are neutralized and removed as organic acid salts with entrained organic acid alkyl esters. This mixture can be acidulated to generate an organic acid/alkyl ester mix, not unlike the mixture originating from base catalytic glycerin, that can serve as feedstock for the first reaction method.

First Reaction Method—Low Pressure (Less than (<) about 20 Barg) Esterification (with or without Transesterification) Via Alkylating Reagent In alternative embodiments, the feedstock containing organic acid is subjected to a first reaction method that generates a first reaction product mixture of organic acid alkyl esters with organic acid content less than about 5 wt % or between about 1 wt % and 10 wt %. In alternative embodiments the first reaction method is a relatively low pressure (less than (<) about 20 barg, or about 300 psig; or less than about 15 barg) approach that contacts the feedstock over many hours with one or more alkylating reagents. The alkylating reagent can be chosen from alcohol, alkyl carbonate, alkyl ether, alkyl ester, or alkyl sulfate. In alternative embodiments, the alkylating reagent an alcohol, optionally methanol and/or ethanol.

In alternative embodiments, the first reaction method utilizes one or multiple stages or vessels in which the feedstock is heated to a temperature between 100 to 400° C., optionally at 150 to 300° C., then contacted with alkylating reagent for up to 12 hrs per stage, optionally no more than about 8 hrs (or between about 5 to 20 hours) per stage, while maintaining a pressure between about 11 to 20 barg, optionally up to 355 barg, or between about 10 and 340 to 360 barg.

In alternative embodiments, the last stage 'n' is typically of lower pressure than the previous stage 'n+1' so as to allow for enough pressure gradient to transfer alkylating reagent vapor from one stage to the next. In alternative embodiments, the maximum alcohol:feedstock mass ratio across all vessels/stages is 5:1, or optionally less than 3:1.

In alternative embodiments, to maximize alkylating reagent efficiency and to reduce energy use for excess alkylating reagent recovery, two or more vessels/stages are used. In alternative embodiments, agitation is achieved by bubbling, sparging, stirring, pumping, or a combination thereof. In alternative embodiments, the driest alkylating reagent is contacted with the last stage or vessel material with the lowest organic acid content so as to push the reaction equilibrium forward and achieve the lowest organic acid content desirable. In alternative embodiments, the excess alkylating reagent (which optionally can contain some amount of byproduct water from esterification and possibly glycerin if transesterification also occurs) is then contacted with the material of the next stage or vessel. In alternative embodiments, the wet alkylating reagent vapor leaving the last stage or vessel in the reaction train is purified to recovery alkylating reagent for reuse. In alternative embodiments, the organic acid content of the first reaction method product is less than about 5 wt % or is between about 1 wt % and 10 wt %. In alternative embodiments, the organic acids contained in the feedstock can contain between about 2 to 52 carbons, or can contain about 2, 3, 4, 5, 6, 7 or 8 or more carbons.

In alternative embodiments, at least a portion of the feedstock contains a mixture of organic acid and organic acid alkyl ester isolated from glycerin that originates from the second reaction method. In alternative embodiments the glycerin is derived from the bottom layer of the decanters utilized after each base catalyzed transesterification reactor. In alternative embodiments the bottom layers comprise unreacted alcohol, glycerin, catalyst, and organic acid salt.

In alternative embodiments, to purify the glycerin, it is neutralized with acid, for example HCl, and decanted to separate any lipophilic components, for example organic acid/ester. This lipophilic stream is of low value due to its mixed nature and can be valorised into higher value organic acid alkyl esters by fully converting the organic acids that remain after acidulation of glycerin.

In alternative embodiments, to increase the reaction kinetics of the first reaction method, a pressure loop with smaller volume (less than (<) about 20%) than the main vessel may be employed. In alternative embodiments, this pressure loop is outfitted with a pump and back pressure control device, and optionally a heat input device/exchanger and/or hydrodynamic cavitation device. In alternative embodiments, some or all of the alkylating reagent being fed to a vessel or stage is introduced downstream of a pressure loop pump. In alternative embodiments, the pressure loop operates at a pressure where the reaction kinetics factor increase over the main vessel reaction kinetics meets or exceeds the volume ratio between the vessel:loop ratio so that the reaction rate gain is worth the additional capital expense for a higher pressure section. In alternative embodiments, the operating pressure range of the loop is between about 2% and about 1200% above that of the main vessel, alternatively between about 100% to about 1200%.

It is well-known that supercritical fluids are generally more superior in mass transfer and reaction kinetics. In alternative embodiments, to maximize the reaction kinetics of the pressure loop, the temperature and pressure should exceed the critical point (or critical temperature and pressure) of the alkylating reagent being used, for example, about 239° C. and 81.1 barg for methanol. In alternative embodiments, the alkylating reagent is introduced downstream of the pressure loop pump and before the heat input device/exchanger. In alternative embodiments, glycerides are present and/or are added, then the rate of transesterification is also greatly enhanced in addition to the rate of esterification. In alternative embodiments, a hydrodynamic cavitation device is employed to minimize the volume of the pressure loop and/or to further increase the reaction kinetics, thus providing potential capital savings.

In alternative embodiments, to push the reaction equilibrium closer to full conversion of organic acids to organic acid alkyl esters, alkylating reagents other than alcohol are used in conjunction or separately. In alternative embodiments, to not upset the alkylating reagent recovery section, the amount and type of additional alkylating reagent(s) chosen is compatible. In alternative embodiments, the alternative non-alcohol alkylating reagent is an alkyl carbonate, for example methyl carbonate.

In alternative embodiments, one or multiple types of catalysts are used to enhance reaction kinetics of the first reaction method. The catalyst may be organic or inorganic, alternatively or optionally a liquid metal catalyst that is soluble in the reaction medium. In alternative embodiments, an alternative type of liquid metal catalyst used is an organic acid salt, which can be of any valence. In alternative embodiments, the organic acid salt is an alkaline earth metal salt of an aliphatic organic acid. In alternative embodiments, the alkaline earth metal is magnesium and/or calcium. In alternative embodiments, the aliphatic organic acid has between about 4 to 52 carbon atoms or 2 to 20 carbon atoms. The alkaline earth metal liquid metal catalyst may be formed and added before or during the first reaction method.

In alternative embodiments, the product mixture generated by the first reaction method is referred to as the "first reaction method or process product".

In alternative embodiments, the acid value of the first reaction method product is less than 5, alternatively or optionally less than 1.

In alternative embodiments, the first reaction method is conducted with or without catalyst. In alternative embodiments, the first reaction method is conducted without catalyst.

In alternative embodiments, the first reaction method or process product is subjected to one or more processing steps to generate one or more derivatives of the first reaction method or process product. In alternative embodiments, the first reaction method product is subjected to neutralization and/or desolventizing before transitioning to the second reaction method. In alternative embodiments, the first reaction method product is subjected to neutralization and/or desolventizing before transitioning to downstream purification to produce an organic acid alkyl ester stream of 95 wt % purity or higher, or between 90 wt % and 99.5 wt % purity.

In alternative embodiments, the manner or industrial configuration that the first reaction method or process is conducted is batch, semi-batch, semi-continuous, continuous, or a combination thereof.

In alternative embodiments, the catalyst used for the first reaction method or process (if a catalyst is used) is acidic. For example, in alternative embodiments, the acidic catalyst comprises a Lewis acid, a heterogeneous acid, an inorganic acid, an organic acid or any combination thereof. In alternative embodiments, if heterogeneous acid is used, then it can be employed as a slurry, a packed bed, a contained catalyst basket or any combination thereof.

In alternative embodiments, the catalyst used for the first reaction method is basic. For example, in alternative embodiments, the base catalyst comprises an oxide, an alkoxide, a hydroxide, carbonate or an amine or any combination thereof. In alternative embodiments, the base catalyst is a monovalent alkoxide, for example, a sodium or potassium methoxide.

In alternative embodiments, the first reaction method or process is conducted in one vessel employing one or multiple stages. In alternative embodiments, the first reaction method or process is conducted in multiple vessels employing one stage per vessel. In alternative embodiments, the first reaction method or process is conducted in multiple vessels employing multiple stages per vessel. In alternative embodiments, a "stage" is defined as a length of time between 1 second to 72 hours in which the temperature, pressure and flowrate of alkylating reagent are fixed but wherein the organic acid content is reduced by at least 0.05 wt % (or is reduced by between about 0.10 wt % and 0.025 wt %) by the end of the stage.

Second Reaction Method—Transesterification (Catalytic or Enzymatic)

In alternative embodiments, the first reaction process or method product contains glycerides (for example, a triacylglyceride) and/or other saponifiables (such as, for example, a wax, a glycerophospholipid, a triglyceride, a diglyceride, a monoglyceride or a sphingolipid or a combination thereof) that require catalytic or enzymatic transesterification to be converted into organic acid alkyl esters.

In alternative embodiments, the catalyst used for the second reaction process or method is acidic. For example, in alternative embodiments, the acidic catalyst comprises a Lewis acid, a heterogeneous acid, an inorganic acid, an organic acid or any combination thereof. In alternative embodiments, if heterogeneous acid is used, then it can be employed as a slurry, a packed bed, a contained catalyst basket or any combination thereof.

In alternative embodiments, the catalyst used for the second reaction process or method is basic. For example, in alternative embodiments, the base catalyst comprises an oxide, an alkoxide, a hydroxide, carbonate or an amine or any combination thereof. In alternative embodiments, the base catalyst is a monovalent alkoxide, for example, a sodium or potassium methoxide.

In alternative embodiments, the first reaction method or process product contains less than about 5 wt % organic acid that is neutralized by base to less than about 0.5 wt % organic acid prior to the onset of the transesterification reaction.

In alternative embodiments, the neutralized organic acid forms an organic acid salt that can remain in the neutralized mixture or can be separated prior to the onset of the transesterification reaction. The compound used to neutralize organic acids may be virgin, for example, sodium hydroxide or alkoxide from a vendor, or it can be recycled, for example, it can be a hydroxide or alkoxide from, for example, a crude glycerin prior to acidification.

In alternative embodiments, the transesterification reaction occurs in one or multiple vessels and/or stages. The residence time inside each vessel or stage can be up to 24 hours, or between about 20 to 30 hours (hrs), with a maximum alcohol:neutralized mixture mass ratio of 10:1 in any individual stage. The maximum reaction temperature cannot exceed about 240° C., with an alternative reaction temperature between about 60° C. to about 100° C.

In alternative embodiments, the first reaction method or process product or any of its derivatives is subjected to transesterification and converted into a second reaction method or process product that contains less than about 1 wt % glyceride (or between about 0.25 to 3 wt %) glyceride content. In alternative embodiments, to generate this second reaction method or process product, the following compounds are removed (or substantially removed, for example, between about 95% to 99% removed) by any combination of decantation, washing and/or desolventizing: organic acid salts, glycerin, alcohol and water. If required or desired, the second reaction method or process product is subjected to purification to generate an organic acid alkyl ester stream of about 95 wt % ester content or greater (or between about 90 to 99 wt % ester content), optionally meeting the B100 biodiesel specification.

In alternative embodiments, the second reaction method or process comprises two transesterification reactors and three decanters. The first reactor converts any residual organic acids into organic acid salts, or substantially converts (or converts 95% or greater, or converts between about 90% to 99.5%) residual organic acids into organic acid salts. In alternative embodiments, the first reactor also converts a majority, or optionally about 90% or more, or between about 85% to 99%, of glycerides into organic acid alkyl esters. In alternative embodiments, the first decanter removes (or substantially removes) a majority of (or between about 85% to 99% of) glycerin that was freed by transesterification in the first reactor from the organic acid alkyl ester phase, along with a majority of (or between about 85% to 99% of) unreacted alcohol. In alternative embodiments, the second reactor converts virtually all of (or between about 95% to 99.5% of) the remaining glycerides remaining in the organic acid alkyl ester phase into organic acid alkyl esters. The second decanter removes a majority of (or between about 90% to 99.5% of) glycerin and methanol present after the second reactor. In alternative embodiments, after the second decanter, the organic acid alkyl ester phase is washed with water to capture residual glycerin, base catalyst and organic acid salt, then sent to a third decanter to remove (or substantially remove, or remove between about 90% to 99.5% of) the aqueous phase from the washed organic acid alkyl esters.

In alternative embodiments, the first reaction method or process product or any of its derivatives is combined with one or multiple reactors or decanters within the second reaction or process method.

In alternative embodiments, the second reaction method utilizes the glyceride-heavy stream deficient in organic acids, or "steam stripper heavies", that was generated by steam stripping of the original feedstock (which optionally comprises about 20 wt % or less organic acids, or 1% to 20 wt % organic acids). In alternative embodiments, the first reaction method or process product or any of its derivatives that is combined into the second reaction method or process partially or fully originates from the organic acid-heavy stream, or "steam stripper lights", that was generated from the original feedstock containing (which optionally comprises about 20 wt % or less organic acids, or 1% to 20 wt % organic acids).

Purification of Organic Acid Alkyl Esters

In alternative embodiments, the first reaction method or process product or any of its derivatives and/or the second reaction method or process product or any of its derivatives proceed(s) to one or more separation steps wherein a majority (or between about 95% to 99.5%) or all of the organic acid alkyl esters are separated from the other compounds present in the stream, for example organic acid salts, waxes, glycerides, organic acids, tocopherols, or sterols, or the like to yield a first organic acid alkyl ester stream comprising substantially pure for example 95% or more, or between about 90% and 99.5%, organic acid alkyl esters. In alternative embodiments, these separation steps comprise decantation, centrifugation, evaporation, distillation, crystallization, liquid-liquid extraction, chromatography, adsorption, and/or ion exchange, or any combination thereof.

In alternative embodiments, the first reaction method product is desolventized to remove (or substantially remove, or remove between about 90% and 99.5% of) alkylating reagent remaining after the first reaction method. This desolventized derivative of the first reaction method product can optionally meet the B100 specification or be further purified until it meets the B100 specification.

In alternative embodiments, the first reaction method or process product is first desolventized to remove (or substantially remove, or remove between about 90% and 99.5% of) alkylating reagent remaining after the first reaction method, then purified to generate an organic acid alkyl ester stream of 95 wt % purity or higher (or substantially purify to between about 90 wt % and 99.5 wt % purity).

In alternative embodiments, the final separation step for producing a stream containing 95 wt % or more (or between about 90 wt % and 99.5 wt %) organic acid alkyl esters comprises a distillation, for example, as a distillation column. In alternative embodiments, the distillation column comprises a packed distillation column or a trayed distillation column. In alternative embodiments, the distillation column comprises between 1 and 50 stages, for example between 5 and 45 stages, between 10 and 40 stages, between 15 and 35 stages, between 20 and 30 stages, or 25 stages.

In alternative embodiments, the distillation is conducted under a vacuum in the range of between about 0.1 and 200 Torr absolute, for example between about 2 and 150, between 4 and 100, between 6 and 50, between 8 and 20, or about 10 Torr absolute.

In alternative embodiments, where methanol is the alcohol used in the esterification/transesterification reaction, the distillate stream comprises substantially pure (between about 90 wt % and 99.5 wt % pure) fatty acid methyl ester (FAME) meeting or exceeding the standards established for ASTM B100-grade biodiesel. In alternative embodiments, if the distillate does not meet the B100 specification, it can be chemically neutralized to effectively reduce the acid value to meet the B100 specification. In alternative embodiments, at least a portion of (or between about 1% to 50% of) the purification residuals material is sent to one or more additional separation steps to valorize one or multiple components in the stream.

In alternative embodiments, the "bottoms" of the distillation column, or purification residuals, from the organic acid alkyl ester distillation step can comprise, for example, organic acid salts, unreacted esters, for example glycerides any combination of mono-glycerides, di-glycerides, and triglycerides), sterols, tocopherols, and various unsaponifiable material for example waxes and hydrocarbons.

In alternative embodiments, some or all organic acid alkyl esters are separated (or substantially separated, or between about 90% to 99% separated) from saponifiables and/or unsaponifiables to create a "first organic acid alkyl ester" and a "purification residuals phase". Any method and/or process known in the art may be used to effect this separation. Some examples of separation methods include, but are not limited to: distillation, chromatography, ion exchange, crystallization, liquid-liquid extraction, and the like.

In alternative embodiments, the first organic acid alkyl ester generated meets commercial biodiesel specifications that allow for its sale in the market as specification-grade biodiesel.

In alternative embodiments, the first organic acid alkyl ester generated does not meet commercial biodiesel specifications. Any number of additional upgrading techniques may be used to generate a material that does meet commercial biodiesel specifications that allow for its sale in the market as specification-grade biodiesel.

In alternative embodiments, the saponifiables and/or unsaponifiables in the purification residuals phase remaining after some or all organic acid alkyl esters are separated can comprise a range of organic acid salts and/or glycerides (for example, between about 0% and 15%, or 0.5%, 1%, 2%, 3%, 4%, 5%, 10% or 20% or more, of glycerides), and, for example, the glycerides can comprise glycerides that were not transesterified to generate fatty acids esters, for example, wherein the amount of glycerides that were not transesterified to generate fatty acid esters comprise between about 0 wt % and 100 wt %, or between about 0.5 wt % and 70 wt %, or between about 1 wt % and 60 wt %, or between about 5 wt % and 50 wt %, or between about 10 wt % and 40 wt %, or about 10, 15, 20, 25, 30, 35, 40, 45 or more wt % of the saponifiables.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the following examples; however, it is to be understood that the exemplary embodiments provided herein are or the invention are not limited to such examples.

EXAMPLES

Example 1—Exemplary Low Pressure Alcoholysis Process

This example describes an exemplary low pressure alcoholysis process as provided herein.

900 grams (g) of oleic acid (AV 192) is heated to 205 C in a 1.9 L stirred autoclave reactor, then contacted with 600 gram (g) 98/2 weight methanol-water over a 4 hour (hr) period while maintaining constant pressure of 12 barg. The material is sampled and assayed to have an AV of 7.5. The autoclave material is then heated to 245° C. and contacted with 1200 g 99.9% methanol over a 12 hr period while maintaining constant pressure of 13 barg. This material is assayed to have an AV of less than (<) 0.4.

Example 2—Exemplary Low Pressure Alcoholysis

This example describes a further, alternative exemplary low pressure alcoholysis process as provided herein.

900 g of 75/25 weight oleic acid-fatty acid distillate (for example, an animal fat) is heated to 205° C. in a 1.9 L stirred autoclave reactor, then contacted with 600 g 98/2 weight methanol-water over a 4 hr period while maintaining constant pressure of 12 barg. The material is sampled and assayed to have an AV of 8.3. The autoclave material is then heated to 245° C. and contacted with 1200 g 99.9% methanol over a 12 hr period while maintaining constant pressure of 13 barg. This material is assayed to have an AV of less than (<) 0.8.

Example 3—Exemplary Low Pressure Alcoholysis

This example describes a further, alternative exemplary low pressure alcoholysis process as provided herein.

900 g of brown grease (AV 165) is heated to 205 C in a 1.9 L stirred autoclave reactor, then contacted with 600 g 98/2 weight methanol-water over a 4 hr period while maintaining constant pressure of 12 barg. The material is sampled and assayed to have an AV of 6.2. The autoclave material is then heated to 245 C and contacted with 1200 g 99.9% methanol over a 12 hr period while maintaining constant pressure of 13 barg. This material is assayed to have an AV of less than (<) 0.5.

Example 4—Exemplary Low Pressure Alcoholysis

This example describes a further, alternative exemplary low pressure alcoholysis process as provided herein.

900 g of soy acid oil (AV 120) is heated to 205° C. in a 1.9 L stirred autoclave reactor, then contacted with 600 g 98/2 weight methanol-water over a 4 hr period while maintaining constant pressure of 12 barg. The material is sampled and assayed to have an AV of 5.6. The autoclave material is then heated to 245° C. and contacted with 1200 g 99.9% methanol over a 12 hr period while maintaining constant pressure of 13 barg. This material is assayed to have an AV of less than (<) 0.7.

Example 5—Exemplary Process for Base Catalyzed Transesterification of Low Pressure Alcoholysis Product This example describes an exemplary process for base catalyzed transesterification of low pressure alcoholysis product.

900 g of material generated from Example 3 (glyceride content 20 wt %) is combined with 100 g methanol and 8 g sodium methoxide into a 1.9 L stirred autoclave reactor, then heated to 65° C. and maintained for 30 minutes (min). The material is decanted for 2 hrs and bottom layer is removed. The top layer is combined with 100 g methanol and 4 g sodium methoxide, heated to 65° C. and maintained for 30 min. This material is decanted for 2 hrs and bottom layer removed. This top layer is water washed and neutralized to pH 7, then dried to less than (<) 0.1 wt % moisture. The final product has glyceride content of less than (<) 0.1 wt % and organic acid alkyl ester content of 96%.

Example 6—Exemplary Base Catalyzed Transesterification of Low Pressure Alcoholysis Product This example describes an exemplary process for base catalyzed transesterification of low pressure alcoholysis product.

900 g of material generated from Example 4 (glyceride content 45 wt %) is combined with 100 g methanol and 8 g sodium methoxide into a 1.9 L stirred autoclave reactor, then heated to 65 C and maintained for 30 min. The material is decanted for 2 hrs and bottom layer is removed. The top layer is combined with 100 g methanol and 4 g sodium methoxide, heated to 65° C. and maintained for 30 min. This material is decanted for 2 hrs and bottom layer removed. This top layer is water washed and neutralized to pH 7, then dried to less than (<) 0.1 wt % moisture. The final product has glyceride content of less than (<) 0.1 wt % and organic acid alkyl ester content of 97%.

What is claimed is:

1. A method or an industrial process for producing an organic acid alkyl ester comprising:
   conducting an esterification reaction between:
   (i) a feedstock comprising an organic acid; and,
   (ii) an alkylating reagent, with or without catalyst,
   wherein the esterification reaction conditions comprise a temperature of between about 100° C. to 400° C. and a pressure of between about 0.1 barg to 355 barg, to generate the organic acid alkyl ester which may comprise unreacted or remaining saponifiables,
   wherein the alkylating reagent comprises one or multiple alkylating compounds or reagents,
   wherein the one or multiple alkylating compounds or reagents comprises: a monohydric alcohol, a polyhydric alcohol, an alkyl carbonate, an alkyl sulfate, an alkyl ether, an alkyl sulfate, an alkyl halide, an alkyl ester or a combination thereof, and
   wherein the minimum amount of organic acid contained in the feedstock is about 50 parts per million (ppm), or between about 45 to 55 ppm, or between about 40 to 60 ppm,
   and wherein the esterification reaction takes place in
   at least one pressurized vessel or stage and a pumparound pressure loop,
   wherein the at least one pressurized vessel or stage is incorporated into the pumparound pressure loop, and the pumparound pressure loop operates at a higher pressure than the pressurized vessel or stage such that products that leave the pressurized vessel or stage are continuously circulated back to the pressurized vessel or stage through the pumparound pressure loop, wherein the reaction rate within the pumparound pressure loop is higher than within the pressurized vessel or stage, wherein the relative volume of the pumparound pressure loop is less than or equal to about 20%, or less than or equal to about 10% and 50%, of the pressurized vessel or stage volume, and wherein the relative pressure of the pumparound pressure loop is at least about 2% greater, or at least between about 0.5% and 5% greater, than the operating pressure of the pressurized vessel or stage.

2. The method or industrial process of claim 1, further comprising desolventizing and/or neutralizing the organic acid alkyl ester to generate desolventized and/or neutralized organic acid alkyl ester products.

3. The method or industrial process of claim 1, wherein: the alkyl chain or the alkylating reagent comprises 1, 2, 3, 4, 5 or 6 carbons: or, the alkyl carbonate, alkyl sulfate, alkyl ether, alkyl sulfate, alkyl halide or alkyl ester comprises a methyl carbonate, methyl sulfate, methyl ether, methyl sulfate, methyl halide or methyl ester, respectively; or an ethyl carbonate, an ethyl sulfate, an ethyl ether, an ethyl sulfate, an ethyl halide or an ethyl ester, respectively.

4. The method or industrial process of claim 1, wherein if a catalyst is present, the catalyst comprises a base catalyst.

5. The method or industrial process of claim 4, wherein the base catalyst, if present, comprises: an oxide, an alkoxide, a hydroxide, a carbonate or an amine or any combination thereof.

6. The method or industrial process of claim 5, wherein the alkoxide base catalyst, if present, comprises a monovalent alkoxide base catalyst.

7. The method or industrial process of claim 6, wherein the monovalent alkoxide catalyst, if present, comprises a sodium or potassium methoxide.

8. The method or industrial process of claim 5, wherein the hydroxide base catalyst, if present, comprises sodium hydroxide.

9. The method or industrial process of claim 1, wherein the feedstock comprises greater than about 10%, or between about 5% to 10%, or between about 2% to 20%, of one or multiple organic acids.

10. The method or industrial process of claim 9, wherein the organic acid comprises one or a multiple of carboxylic acids or fatty acids.

11. The method or industrial process of claim 1, wherein the feedstock comprises one or multiple organic acids and/or one or multiple saponifiable compounds.

12. The method or industrial process of claim 11, wherein the one or multiple saponifiable compounds comprises a wax, a triacylglyceride, a diglyceride, a monoglyceride, a glycerophospholipid or a sphingolipid or a combination thereof.

13. The method or industrial process of claim 1, wherein the feedstock comprises:
a soft seed acid oil, or a soft seed acid oil originating from a direct acidulation of a soft seed soapstock;
a brown grease, or a brown grease originating from a fat, oil or grease (FOG) effluent;
a Soap Carbonate Technology (SCT) product; and/or
an organic acid, or an organic acid and alkyl ester mixture, or an organic acid originating from acidulation of glycerin separated from base catalytic transesterification reaction mixtures.

14. The method or industrial process of claim 1, wherein the alcohol comprises an alcohol having between 1 and 5 carbons, or 1, 2, 3, 4, 5, 6, 7 or 8 or more carbons, or the alcohol comprises: methanol, ethanol, propanol, butanol, isobutanol, isopropyl alcohol or a combination thereof.

15. A method or an industrial process for producing an organic acid alkyl ester product from a feedstock,
wherein the feedstock comprises about 50 weight percent (wt %) or less, or between about 50 wt % and 5 wt %, or between about 50 wt % and 50 ppm, organic acid, with or without a catalyst,
the method comprising:
a separation process comprising:
(a) steam or gas stripping of the feedstock to generate:
(i) a first stream comprising about 50 wt % or more organic acid content, wherein optionally the organic acid comprises a fatty acid; and,
(ii) a second stream comprising about 5 wt % or less organic acid content, and optionally the second stream comprises glyceride,
wherein the first stream and the second stream are separated under conditions comprising atmospheric pressure or vacuum pressure at a temperature of between about 150° C. to 280° C., while feeding nitrogen or steam into the feedstock being stripped,
(b) separately reacting the separated streams:
(i) reacting the first stream using a first reaction process with or without a catalyst to esterify and reduce the organic acid value to less than about to generate a first reaction process product,
wherein the first reaction process comprises countercurrently contacting the first stream with an organic alkylating reagent over two or more vessels or stages at a temperature between about 100° C. and 400° C. and pressure between about barg and 355 barg while simultaneously removing water and/or glycerin with unreacted alkylating reagent from the final vessel or stage to result in the organic acid alkyl ester product which may comprise unreacted or remaining saponifiables; and,
(ii) reacting the second stream comprising glyceride using a second reaction process to transesterify and generate a second reaction process product with glyceride content of about 5 wt % or less, or optionally to about 1 wt % or less,
thereby generating a first and a second reaction process product; and
(c) combining the first reaction process product into the second reaction process product at any point in the process to neutralize any unreacted or residual organic acids and to transesterify and convert any unreacted or remaining glycerides into organic acid alkyl esters via the second reaction process, thus adding to the mass of the second reaction process product,
and wherein the first reaction process comprising the esterification reaction takes place in
at least one pressurized vessel or stage and a pumparound pressure loop,
wherein the at least one pressurized vessel or stage is incorporated into the pumparound pressure loop, and the pumparound pressure loop operates at a higher pressure than the pressurized vessel or stage such that products that leave the pressurized vessel or stage are continuously circulated back to the pressurized vessel or stage through the pumparound pressure loop, wherein the reaction rate of the esterification process within the pumparound pressure loop is higher than the reaction rate of the esterification process within the pressurized vessel or stage, wherein the relative volume of the pumparound pressure loop is less than or equal to about 20%, or less than or equal to about 10% and 50%, of the pressurized vessel or stage volume, and wherein the relative pressure of the pumparound pressure loop is at least about 2% greater, or at least between about 0.5% and 5% greater, than the operating pressure of the pressurized vessel or stage but no more than about 1200% or between about 1000% and 1400%.

16. The method or industrial process of claim 1, wherein the transesterification reaction converts at least about 5%, 10%, 15%, 20% or 25% of the unreacted or remaining saponifiables contained in the organic acid alkyl ester product into organic acid alkyl esters.

17. The method or industrial process of claim 1, wherein the one or more saponifiable compound comprises a glyceride or a natural wax.

18. The method or industrial process of claim 1, further comprising subjecting the first reaction process product to one or more purification processes to generate an organic acid alkyl ester stream of about 95 weight percent (wt %) or greater, or between about 80 wt % and 99 wt %, wherein optionally, the first reaction process product is sufficiently low in residual organic acids, or has less that about 1 wt % organic acids, or has between about 0.25 wt % and 2 wt % organic acids, such that the first reaction process product can be purified by distillation to generate organic acid alkyl esters that meet B100 specifications.

19. The method or industrial process of claim 1, wherein the organic acid alkyl ester product is subjected to a transesterification reaction to convert the unreacted or remaining saponifiables into organic acid alkyl esters, and wherein any residual organic acid content in the organic acid alkyl ester product is neutralized by the same base catalyst used during transesterification if a base catalyst is used.

20. The method or industrial process of claim 1, wherein: the pumparound pressure loop utilizes hydrodynamic cavitation to intensify reaction kinetics.

21. The method or industrial process of claim 19, wherein at least a portion of the feedstock comprises a mixture of organic acid and organic acid alkyl ester isolated from glycerin that originates from the transesterification reaction.

22. The method or industrial process of claim 15, wherein the catalyst used in the first reaction process or the second reaction process comprises a base catalyst.

23. The method or industrial process of claim 22, wherein the base catalyst, if present, comprises: an oxide, an alkoxide, a hydroxide, a carbonate or an amine or any combination thereof.

24. The method or industrial process of claim 23, wherein the alkoxide base catalyst, if present, comprises a monovalent alkoxide base catalyst, or the alkoxide base catalyst comprises a sodium or potassium methoxide.

25. The method or industrial process of claim 1, wherein no catalyst is used.

26. The method or industrial process of claim 15, wherein no catalyst is used in the first reaction process, or no catalyst is used in the second reaction process.

27. The method or an industrial process of claim 15, wherein the second reaction process further comprises separating the reaction product.

28. The method or an industrial process of claim 27, wherein the second reaction process further comprises separating the reaction product using centrifugation and/or decantation.

29. The method or an industrial process of claim 28, wherein the decantation is under conditions comprising: 100° C. or less, or between 90° C. and 35° C. about, for up to 8 hrs, or between about 1 to 12 hours.

30. The method or industrial process of claim 1, wherein the esterification reaction conditions comprise reacting for between about 1 second and 72 hours, or 1 minute and 48 hours, or 5 minutes and 25 hours.

31. The method or industrial process of claim 1, wherein if a catalyst is present, the catalyst comprises a heterogeneous acid catalyst that is insoluble in a reaction medium.

32. The method or industrial process of claim 15, wherein the catalyst used in the first reaction process or the second reaction process comprises a heterogeneous acid catalyst that is insoluble in a reaction medium.

33. The method or industrial process of claim 15, wherein the transesterification reaction of the second reaction process comprises use of an enzyme or a base catalyst, and having 10% wt % or less catalyst or enzyme in relation to material being reacted, or having between about 1% wt % and 15 wt % catalyst or enzyme in relation to material being reacted, and about 10:1 mass ratio or less alcohol in relation to material being reacted.

34. The method or industrial process of claim 15, wherein the second reaction process comprises use of two transesterification reactors and three decanters.

35. The method or industrial process of claim 19, wherein the transesterification reaction converts at least between about 1% to 50% of the remaining saponifiables contained in the organic acid alkyl ester first reaction method product into organic acid alkyl esters.

36. The method or industrial process of claim 19, wherein the transesterification reaction is catalyzed by an acid or base and utilizes one or more alcohols as reactant.

37. The method or industrial process of claim 13, wherein the SCT product comprises one or a plurality of organic acids generated by thermal hydrolysis or saponification of soapstock, followed by acidulation with optional purification.

38. The method or industrial process of claim 15, wherein separately reacting the separated streams comprises reacting the first stream using a first reaction process with or without a catalyst to reduce the acid value to less than about 5 to generate a first reaction process product.

39. The method or industrial process of claim 1, wherein the feedstock containing organic acids also comprises one or more saponifiable compounds, wherein during and/or after the esterification reaction at least a portion of the one or more saponifiable compounds are converted to an organic acid alkyl ester via a transesterification reaction, and if glyceride is present, at least a portion of the glycerin formed during the transesterification is removed with an excess alkylating reagent in a vapor phase.

40. The method of claim 39, wherein the saponifiable compounds comprise glyceride.

41. The method of claim 15, wherein the feedstock containing organic acids also comprises one or more saponifiable compounds, and during and/or after the esterification reaction at least a portion of the one or more saponifiable compounds are converted to an organic acid alkyl ester via a transesterification reaction, and if glyceride is present, glycerin formed during the transesterification is removed with excess alkylating reagent in a vapor phase.

42. The method of claim 41, wherein the saponifiable compounds comprise glyceride.

43. The method of claim 1, wherein between about 1 and 50% of the alkylating reagent is introduced into the pump-around pressure loop to increase reaction kinetics due to a higher molar ratio of organic reagent to saponifiable content.

44. The method of claim 43, wherein between about 5% and 20% of the alkylating reagent is introduced into the pumparound pressure loop to increase reaction kinetics due to a higher molar ratio of organic reagent to saponifiable content.

45. The method of claim 1 the alkylating reagent is at or above a critical point of the alkylating reagent.

46. The method of claim 45, wherein the alkylating reagent is methanol and the critical point of the methanol is about 239° C. and 81.1 barg.

* * * * *